US007884262B2

(12) United States Patent
Clemente et al.

(10) Patent No.: US 7,884,262 B2
(45) Date of Patent: Feb. 8, 2011

(54) MODIFIED DMO ENZYME AND METHODS OF ITS USE

(75) Inventors: Thomas E. Clemente, Lincoln, NE (US); Razvan Dumitru, Lincoln, NE (US); Paul C. C. Feng, Wildwood, MO (US); Stanislaw Flasinski, Chesterfield, MO (US); Donald P. Weeks, Lincoln, NE (US)

(73) Assignee: Monsanto Technology LLC, St. Louis, MO (US)

( * ) Notice: Subject to any disclaimer, the term of this patent is extended or adjusted under 35 U.S.C. 154(b) by 315 days.

(21) Appl. No.: 11/758,657

(22) Filed: Jun. 5, 2007

(65) Prior Publication Data

US 2008/0015110 A1  Jan. 17, 2008

Related U.S. Application Data

(60) Provisional application No. 60/811,152, filed on Jun. 6, 2006.

(51) Int. Cl.
*A01H 5/00* (2006.01)
*C12N 5/04* (2006.01)
*C12N 15/82* (2006.01)
*C07H 21/04* (2006.01)

(52) U.S. Cl. ........................ 800/278; 800/298; 800/300; 800/300.1; 800/306; 800/312; 800/314; 435/410; 435/412; 435/413; 435/415; 435/418; 536/23.2; 536/23.7

(58) Field of Classification Search ....................... None
See application file for complete search history.

(56) References Cited

U.S. PATENT DOCUMENTS

| | | | |
|---|---|---|---|
| 4,816,403 A | 3/1989 | Roy | 435/253.3 |
| 5,445,962 A | 8/1995 | Atallah et al. | 435/252.1 |
| 5,656,422 A | 8/1997 | Crawford et al. | 435/4 |
| 5,670,454 A | 9/1997 | Grossmann et al. | 504/244 |
| 5,850,019 A | 12/1998 | Maiti et al. | 800/317.3 |
| 7,022,896 B1 | 4/2006 | Weeks et al. | 800/300 |
| 7,105,724 B2 | 9/2006 | Weeks et al. | 800/300 |
| 2003/0115626 A1 | 6/2003 | Weeks et al. | 800/300 |
| 2003/0135879 A1 | 7/2003 | Weeks et al. | 800/278 |
| 2008/0119361 A1 | 5/2008 | Feng et al. | 504/105 |
| 2008/0120739 A1 | 5/2008 | Wan et al. | 800/300 |
| 2008/0305952 A1 | 12/2008 | Arnevik et al. | 800/300 |
| 2009/0029861 A1 | 1/2009 | Feng et al. | 800/300 |
| 2009/0081760 A1 | 3/2009 | D'Ordine et al. | 435/189 |
| 2009/0105077 A1 | 4/2009 | Bhatti et al. | 504/206 |

FOREIGN PATENT DOCUMENTS

| | | |
|---|---|---|
| CA | 2165036 | 6/1996 |
| WO | WO 97/41228 | 11/1997 |
| WO | WO 98/45424 | 10/1998 |
| WO | WO 02/068607 | 9/2002 |
| WO | WO 03/034813 | 5/2003 |
| WO | WO 2005/107437 | 11/2005 |
| WO | 2007/143690 | 12/2007 |
| WO | WO 2007/146706 | 12/2007 |
| WO | WO 2008/048964 | 4/2008 |
| WO | WO 2008/051633 | 5/2008 |
| WO | 2008/105890 | 9/2008 |

OTHER PUBLICATIONS

Behrens et al., "Dicamba resistance: enlarging and preserving biotechnology-based weed management strategies," *Science*, 316(5828):1185-1188, 2007.
Becker et al., "New plant binary vectors with selectable markers located proximal to the left T-DNA border," *Plant Mol. Biol.*, 20:1195-1197, 1992.
Carrington et al., "Cap-independent enhancement of translation by a plant potyvirus 5' nontranslated region," *J. Virology*, 64:1590-1597, 1990.
Cork et al., "Detection, isolation, and stability of megaplasmid-encoded chloroaromatic herbicide-degrading genes within *Pseudomonas* species," *Adv. Appl. Microbiol*, 40:289-321, 1995.
Cork et al., "Microbial transformations of herbicides and pesticides," *Adv. Appl. Microbiol.*, 36:1-66, 1991.
Coruzzi et al., "Nucleotide sequences of two pea cDNA clones encoding the small subunit of ribulose 1,5-bisphosphate carboxylase and the major chlorophyll a/b-binding thylakoid polypeptide ," *J. Biol. Chem.*, 258(3):1399-1402, 1983.
Desvaux et al., "Genomic analysis of the protein secretion systems in *Clostridium acetobutylicum* ATCC 824," *Biochimica et Biophysica Acta*, 1745:223-253, 2005.
Hajdukiewicz et al., "The small, versatile pPZP family of *Agrobacterium* binary vectors for plant transformation," *Plant Mol. Biol.*, 25:989-994, 1994.
Herman et al., "A three-component dicamba O-demethylase from *Pseudomonas maltophilia*, strain DI-6: gene isolation, characterization, and heterologous expression," *J. Biol. Chem.*, 280:24759-24767, 2005.
Hoffman et al., "Type I hyperlipoproteinemia due to a novel loss of function mutation of lipoprotein lipase, Cys(239)—>Trp, associated with recurrent severe pancreatitis," *J. Clin. Endocrinol. Metab.*, 85(12):4795-4798, 2000.
Koncz et al., "The promoter of $T_L$-DNA gene 5 controls the tissue-specific expression of chimaeric genes carried by a novel type of *Agrobacterium* binary vector," *Mol. Gen. Genet.*, 204:383-396, 1986.
Krueger et al., "Isolation and identification of microorganisms for the degradation of dicamba," *J. Agric. Food Chem.*, 37:534-538, 1989.
Mitsuhara et al., "Efficient promoter cassettes for enhanced expression of foreign genes in dicotyledonous and monocotyledonous plants," *Plant Cell Physiol.*, 37:49-59, 1996.

(Continued)

*Primary Examiner*—Eileen B O Hara
(74) *Attorney, Agent, or Firm*—Pamela J. Sisson, Esq.; SNR Denton US LLP

(57) ABSTRACT

The invention provides a modified variant of dicamba monooxygenase (DMO). The invention relates to the unexpected finding that cells expressing this DMO exhibit high levels of tolerance to the herbicide dicamba. Compositions comprising DMO-encoding nucleic acids and methods of use are provided.

24 Claims, 18 Drawing Sheets

OTHER PUBLICATIONS

Svab et al., "Aminoglycoside-3"-adenyltransferase confers resistance to spectinomycin and streptomycin in *Nicotiana tabacum*," *Plant Mol. Biol.*, 14:197, 1990.

Svab et al., "Stable transformation of plastids in higher plants," *Proc. Natl. Acad. Sci. USA*, 87(21):8526-8530, 1990.

Wada et al., "Molecular characterization of coagulation factor XII deficiency in a Japanese family," *Thromb. Haemost.*, 90(1):59-63, 2003.

Xiaoman et al., "Study of BRCA1 gene in hereditary breast and ovarian cancer," *Chin. Med. Sci. J.*, 14(4):195-199, 1999.

Khalil et al., "Plasmid-mediated catabolism of dicamba by *Pseudomonsas* species strain PXM," *Microbios*, 102:183-191, 2000.

Spencer et al., "Segregation of transgenes in maize," *Plant Molecular Biology*, 18:201-210, 1992.

Weeks et at, "Characterization of a bacterial system capable of degrading dicamba and evaluation of its potential in the development of herbicide-tolerant crops," *J. of Cellular Biochemistry*, Supplement 18A:91, 1994.

"Banvel Herbicide," In: Crop Protection Reference, 11$^{th}$ Edition, pp. 1803-1821, 1995.

Al-Khatib et al., "Foliar absorption and translocation of dicamba from aqueous solution and dicamba-treated soil deposits," *Weed Technology*, 6:57-61, 1992.

Baker, "Response of cotton (*Gossypium hirsutum*) to preplant-applied hormone-type herbicides," *Weed Technology*, 7:150-153, 1993.

U.S. Appl. No. 12/440,173, filed Mar. 5, 2009, Bhatti et al.

Batie et al., "Phthalate dioxygenase reductase and related flavin-iron-sulfur containing electron transferases," In: Chemistry and Biochemistry of Flavoproteins, Muller (Ed.), CRC Press, Boca Raton, FL, pp. 543-556, 1992.

Batie et al., "Purification and characterization of phthalate oxygenase and phthalate oxygenase reductase from *Pseudomonas cepacia*," *J. of Bio. Chem.*, 262(4):1510-1518, 1987.

Bernhardt et al., "A 4-methoxybenzoate O-demethylase from *Pseudomonas putida*. A new type of monoxygenase system," *Eur. J. Biochem.*, 57(1):241-256, 1975.

Butler et al., "Structure-function analysis of the bacterial aromatic ring-hydroxylating dioxygenases," *Advances in Microbial Physiology*, 38:47-85, 1997.

Dehmel et al., "Cloning, nucleotide sequence and expression of the gene encoding a novel dioxygenase involved in metabolism of carboxydiphenyl ethers in *Pseudomonas pseudoalcaligenes* POB310," *Arch. Microbiol.*, 163:35-41, 1995.

Fogarty et al., "Microbiological degradation of the herbicide dicamba," *J. of Industrial Microbiology*, 14:365-370, 1995.

Fukumori et al., "Purification and characterization of 2,-dichlorophenoxyacetate/α-ketoglutarate dioxygenase," *J. Biol. Chem.*, 268:24311-24317, 1993.

Gibson et al., "Aromatic hydrocarbon dioxygenases in environmental biotechnology," *Current Opinion in Biotechnology*, 11:236-243, 2000.

Gurbiel et al., "Active site structure of Rieske-type prteins: electron nuclear double resonance studies of isotopically labeled phthalate dioxygenase from *Pseudomonas cepacia* and Rieske protein from rhodobacter capsulatus and molecular modeling studies of a Rieske center," *Biochemistry*, 35(24):7834-7845, 1996 (Abstract).

Krueger et al., "Use of dicamba-degrading microorganisms to protect dicamba susceptible plant species," *J. of Agri. and Food Chem.*, 39(5):1000-1003, 1991.

Magnusson et al., "Tolerance of soybean (*Glycine max*) and sunflower (*Helianthus annuus*) to fall-applied dicamba," *Weed Sci.*, 35:846-852, 1987.

Markus et al., "Purification and some properties of component A of the 4-chlorophenylacetate 3,4-dioxygenase from *Pseudomonas* species strain CBS," *J. of Biol. Chem.*, 261(27):12883-12888, 1986.

Mason et al., "The electron-transport proteins of hydroxylating bacterial dioxygenases," *Ann. Rev. of Microbiology*, 46:277-305, 1992.

Peniuk et al., "Physiological investigations into the resistance of a wild mustard (*Sinapis arvensis* L.) biotype to auxinic herbicides," *Weed Research*, 33:431-440, 1993.

Sarpe et al., "Researches on resistance of maize hybrids and inbred lines to the herbicides based on 2,4-D and dicamba," *Fragmenta Herbologica Jugoslavica*, 16(1-2):299-305, 1987.

Schroeder et al., "Soft red winter wheat (*Triticum aestivum*) response to dicamba and dicamba plus 2,4-D," *Weed Technology*, 3:67-71, 1989.

Wang et al., "A three-component enzyme system catalyzes the O demethylation of the herbicide dicamba in *Pseudomonas maltophilia* DI-6," *Applied and Environmental Microbiology*, 63(4):1623-1626, 1997.

Wang, "Characterization of cellular and enzymatic degradation of dicamba by *Pseudomonas maltophilia*, Strain DI-6," Thesis, University of Nebraska, Aug. 1996.

Office Action regarding U.S. Appl. No. 11/758,653 dated Dec. 29, 2009.

Office Action regarding U.S. Appl. No. 11/758,656 dated Sep. 15, 2009.

Response to Office Action regarding U.S. Appl. No. 11/758,656 dated Dec. 17, 2009.

Office Action regarding U.S. Appl. No. 11/758,659 dated Nov. 24, 2009.

Sprague, "Avoid herbicide spray tank contamination," *IPM News*, ipmnews.msu.edu/fieldcrop/tabid/56, Mar. 24, 2010.

Thompson et al., "Soybean tolerance to early preplant applications of 2,4-D ester, 2,4-D amine, and dicamba," *Weed Technology*, 21:882-885, 2007.

Office Action regarding U.S. Appl. No. 10/330,662 dated Apr. 18, 2006.

Interview Summary regarding U.S. Appl. No. 10/330,662, dated Sep. 13, 2006.

Declaration of Donald P. Weeks regarding U.S. Appl. No. 10/330,662, dated Oct. 18, 2006.

Amendment and Response to Office Action regarding U.S. Appl. No. 10/330,662, dated Oct. 18, 2006.

Final Office Action regarding U.S. Appl. No. 10/330,662, dated Jan. 10, 2007.

Amendment and Response to Office Action regarding U.S. Appl. No. 10/330,662, dated Jul. 9, 2007.

Amendment regarding U.S. Appl. No. 10/330,662, dated Jul. 20, 2007.

Office Action regarding U.S. Appl. No. 10/330,662, dated Sep. 21, 2007.

Declaration of Donald P. Weeks regarding U.S. Appl. No. 10/330,662, dated Feb. 20, 2008.

Amendment and Response to Office Action regarding U.S. Appl. No. 10/330,662, dated Mar. 20, 2008.

Office Action regarding U.S. Appl. No. 10/330,662, dated Jul. 9, 2008.

Amendment and Remarks regarding U.S. Appl. No. 10/330,662, dated Jan. 9, 2009.

Final Office Action regarding U.S. Appl. No. 10/330,662, dated Apr. 24, 2009.

Amendment and Remarks regarding U.S. Appl. No. 10/330,662, dated Sep. 24, 2009.

Office Action regarding U.S. Appl. No. 10/330,662, dated Jan. 11, 2010.

Interview Summary regarding U.S. Appl. No. 10/330,662, dated Mar. 19, 2010.

Amendment and Remarks regarding U.S. Appl. No. 10/330,662, dated May 4, 2010.

Amendment and Response to Office Action regarding U.S. Appl. No. 11/758,653, dated Mar. 29, 2010.

Final Office Action regarding U.S. Appl. No. 11/758,653, dated Jun. 24, 2010.

Final Office Action regarding U.S. Appl. No. 11/758,656, dated Apr. 14, 2010.

Amendment and Response to Office Action regarding U.S. Appl. No. 11/758,659, dated May 24, 2010.

Office Action regarding U.S. Appl. No. 11/758,660, dated Apr. 28, 2010.

Notice of Allowance regarding U.S. Appl. No. 10/330,662, dated Jul. 12, 2010.

Amendment and Response to Final Office Action regarding U.S. Appl. No. 11/758,653, dated Aug. 16, 2010.

Declaration of Yuechun Wan Under 37 C.F.R. §1.132, dated Aug. 11, 2010, U.S. Appl. No. 10/330,662.

Amendment and Response to Final Office Action regarding U.S. Appl. No. 11/758,656, dated Aug. 16, 2010.

Notice of Allowance regarding U.S. Appl. No. 11/758,659, dated Aug. 3, 2010.

U.S. Appl. No. 12/875,747, Weeks et al., filed Sep. 3, 2010.

Notice of Allowance regarding U.S. Appl. No. 11/758,656, dated Oct. 4, 2010.

Response to Official Action regarding U.S. Appl. No. 11/758,660, dated Sep. 27, 2010.

Notice of Allowance regarding U.S. Appl. No. 11/758,653, dated Oct. 5, 2010.

Rieske domain

| | |
|---|---|
| gi\|487831555 | SDICPHRFAPLHLGKIVDGGCRIQCAYHALEFDGTGACVKNPHGKQKIPAAAKLQAYPVVE |
| gi\|48850840 | ADRCPHRFVPLSRGQR-DGDMMRCGYHGLAFSSSGGCVMNPFTDEALP-LARVEVLPVVE |
| gi\|48849366 | GGRCPHRFAPLGHGSVVDGALM-CPYHGLRFDGDGRCVMNPHPGGHLP-DARQRVYPLVE |
| oxygenase | |
| gi\|675433660 | LDICPHRFAPLSDGILVNGHLQ-CPYHGLEFDGGGQCVHNPHGNGARPASLNVRSFPVVE |
| gi\|67666800 | EDFCPHRGAPLSLGFVRDGVLV-CGYHGLEMGCNGKTAAMPGQ--RVGGFPAIRSFPVVE |
| gi\|175488443 | EDFCPHRGAPLSLGFVRDGVLV-CGYMGLEMGCNGKPAGMPGQ--RVGGFPSIRSFPAVE |
| gi\|67676326 | EDFCPHRGAPLSLGFVRDGHLV-CGYHGLTMKADGKCASMPGQ--RVGGFPCIRQFPVVE |
| gi\|39936681 | EDACWHRLVPLSKGRLEGDTVV-CGYHGLKFNPQGRCTYMPSQE-TINPSACVRSYPVVE |
| gi\|27377501 | EDACWHRLVPLSKGRLEGDTVV-CGYHGLKYNAQGRCTFMPSQE-TINPSACVRAYPVVE |

Non-Haem Fe

| | |
|---|---|
| domain | |
| gi\|487831555 | KHSLIWVWMGEQAAADPSVIPDFSMLDPDSGFQVSRRDWLHMDASYDLVVDNLMDLSHTA |
| gi\|48850840 | KHTGLWFWPGDADRADPALIPDFGFLDVER---PLMRGHLKMDAGYELVTDNLMDLSHAE |
| gi\|48849366 | RHALLWIMMGDAAKADPASIPDFSWLSDPR--WEAVRGATVAEGHFELYSDNILDLSHAN |
| oxygenase | |
| gi\|675433660 | RDALIWIWPGDPALADPGAIPDFGCRVDPA--YRTVGGYGHVDCNYKLLVDNLMDLGHAQ |
| gi\|67666800 | RYGFVWVWMPGDASRADPAALPALTWADDPV--WAHGGGLYHIRCDYRLMIDNLMDLTHET |
| gi\|175488443 | RYGFVVVWWPGDASSADPAKLPALAWAEDPA--WAHGGGLYHIRCDYRLMIDNLMDLTHET |
| gi\|67676326 | RYGFIWVWWPGDPEQADPARIHHLEWAESEA--WAYGGGLYHIQCDYRLMIDNLMDLTHET |
| gi\|39936681 | RHGFIWVWPGDAEQADPDQIPELHWANDPE--WAYGGGLYHINCDYRLMIDNLMDLTHET |
| gi\|27377501 | RHRFVWLWMGDPVLADPVLADPAL VPDMHWNDDPA--WAGDGKTIYAKCDWRLVVDNLMDLTHET |
| | RHRYIWLWMGDPALADPALVPDMHWNHDPA--WAGDGKTIRVNCDYRLVLDNLMDLTHET |

FIG. 18

MODIFIED DMO ENZYME AND METHODS OF ITS USE

This application claims the priority of U.S. Provisional Patent Application 60/811,152, filed Jun. 6, 2006, the disclosure of which is incorporated herein by reference in its entirety.

BACKGROUND OF THE INVENTION

1. Field of the Invention

The invention relates generally to the field of biotechnology. More specifically, the invention relates to modified dicamba monooxygenase enzymes capable of conferring tolerance to the herbicide dicamba in transgenic organisms.

2. Description of the Related Art

Methods for production of field crops, such as corn, soybeans and cotton, have changed dramatically during the past decade due to the introduction of traits such as insect-resistance and herbicide tolerance through use of plant genetic engineering techniques. These changes have resulted in greater productivity per hectare, decreased production costs, greater flexibility and efficiencies in production regimes, decreased pesticide use, and, in the case of insect-resistant cotton, improved farmer health. Transgenic crops have thus gained widespread adoption and are now grown on millions of acres across the world. However, for transgenic crops to continue to be competitive in the market place, new value-added traits will be required.

Although new traits improving the quantity and quality of agricultural and horticultural crops have appeared and will continue to appear at an increasing rate in years to come, demand exists for traits that improve methods for the production of food, feed and other products. For example, while transgenic plants tolerant to treatments with the herbicides glyphosate, bromoxynil, sulphonylureas and other herbicides are presently available, there are gaps in the spectrum of weeds controlled and treatment options that can be addressed through development of additional herbicide-tolerant crops. Moreover, the appearance of weeds resistant to the herbicides noted above, while generally localized and variably contained, impose the need for supplemental or alternative weed control measures.

While transgenic herbicide tolerance has proven valuable in a commercial setting, plants tolerant to other herbicides are therefore needed to avoid over reliance on any single herbicide and to increase options for managing difficult to control weed species. Of particular need is the development of herbicide tolerance for herbicides that are both environmentally friendly and highly effective for controlling weeds. Dicamba is one such example of an effective and environmentally friendly herbicide that has been used by farmers for more than 40 years. Dicamba is especially useful for the control of annual and perennial broadleaf weeds and several grassy weeds in corn, sorghum, small grains, pasture, hay, rangeland, sugarcane, asparagus, turf, and grass seed crops (Crop Protection Reference, 1995). Unfortunately, dicamba can injure many commercial crops and dicot plants such as soybeans, cotton, peas, potatoes, sunflowers, and canola, which are particularly sensitive to even low levels of the herbicide. Despite this, dicamba is highly effective in controlling weed growth and thus an important tool in agriculture.

Recently, a gene encoding dicamba monooxygenase (DMO) was isolated from *Pseudomonas maltophilia* that confers tolerance to dicamba (U.S. Pat. No. 7,022,896). DMO is involved in conversion of herbicidal dicamba (3,6-dichloro-o-anisic acid) to a non-toxic 3,6-dichlorosalicylic acid. This gene is disclosed in U.S. Pat. No. 7,022,896 as providing tolerance to dicamba in plants expressing the DMO gene. However, the development of variants of this gene would be of great benefit. Such variants could potentially have altered expression efficiency under specific environmental conditions. In this manner, a variant could be selected that is optimized for a specific environment in which it is intended to be used, and may exhibit particularly beneficial kinetic features. The variant in particular may exhibit maximum efficiency at different temperatures or pH conditions, and thus could be selected for a particular crop species depending upon intracellular conditions and/or the anticipated crop growing conditions.

SUMMARY OF THE INVENTION

In one aspect, the invention provides an isolated nucleic acid sequence selected from the group consisting of: a) a nucleic acid sequence encoding the polypeptide of SEQ ID NO:1; b) a nucleic acid sequence comprising the sequence of SEQ ID NO:2; and c) a nucleic acid sequence encoding a polypeptide with at least 90% sequence identity to the polypeptide of SEQ ID NO:1, wherein the polypeptide has dicamba monooxygenase activity and comprises cysteine at a position corresponding to amino acid 112 of SEQ ID NO:1. In other embodiments, a DNA vector is provided comprising a DMO encoding nucleic acid described herein operably linked to a promoter. The promoter may be functional in a plant cell. In certain embodiments, the nucleic acid sequence encoding dicamba monooxygenase may be operably linked to a chloroplast transit peptide.

In another aspect, the invention provides a polypeptide sequence with at least 90% identity to SEQ ID NO:1, wherein the polypeptide has dicamba monooxygenase activity and comprises cysteine at a position corresponding to amino acid 112 of SEQ ID NO:1.

In yet another aspect, the invention provides a host cell or tissue transformed with a dicamba monooxygenase encoding nucleic acid described herein. In certain embodiments, the host cell may be a plant cell. In further embodiments, the plant cell may be defined as a dicotyledonous plant cell or a monocotyledonous plant cell. In specific embodiments, the host cell is a soybean, cotton, maize or rapeseed plant cell. In further embodiments, a tissue culture is provided comprising a transgenic cell described herein.

In still yet another aspect, the invention provides a transgenic plant, and progeny thereof, transformed with a dicamba monooxygenase encoding nucleic acid described herein. In certain embodiments, the plant may be defined as a dicotyledonous or monocotyledonous plant. In specific embodiments, the plant is a soybean, cotton, maize or rapeseed plant.

In still yet another aspect, the invention provides a method of producing a dicamba tolerant plant comprising introducing into the plant a transformation construct provided herein. In one embodiment of the method, introducing the transformation construct may be carried out by stably transforming one or more plant cells and regenerating the one or more cells into a dicamba tolerant plant. In another embodiment, the dicamba tolerant plant may be produced by crossing a parent plant with itself or a second plant, wherein the parent plant and/or the second plant comprises the transformation construct and the dicamba tolerant plant inherits the transformation construct from the parent plant and/or the second plant.

In still yet another aspect, the invention provides a method of producing food or feed comprising: a) obtaining a plant of the invention as provided herein or a part thereof; and b) preparing food or feed from the plant or part thereof. In one embodiment of the invention, the plant part is a seed. In certain further embodiments, the food or feed is oil, meal, protein, grain, starch or protein. In other embodiments, the feed comprises a forage or pasture plant such as hay. The invention also provides methods of producing fibers, pharmaceuticals, nutraceuticals, and industrial chemicals, including biofuels, as well as any other product derived from a plant provided herein.

In still yet another aspect, the invention provides a method of controlling weed growth in a crop growing environment comprising a plant of the invention as provided herein or a seed thereof, comprising applying to the crop growing environment an amount of dicamba herbicide effective to control weed growth. In certain embodiments of the invention, the dicamba herbicide may be applied over the top to the crop growing environment. In specific embodiments, the amount of dicamba herbicide does not damage the plant of the invention or seed thereof and damages a plant of the same genotype as the plant lacking a DMO-encoding nucleic acid provided by the invention.

In still yet another embodiment of the invention, a plant is provided comprising a DMO-encoding nucleic acid provided by the invention and at least one other transgenic coding sequence, including, for example, at least two, three, four, five or more such coding sequences. In particular embodiments, the plants comprise a transgene conferring one or more additional beneficial traits, such as herbicide or pest/insect tolerance. For example, tolerance may be provided to one or more herbicides in addition to dicamba, as well as other beneficial trait, as is described herein below. The invention therefore specifically provides plants comprising a DMO-encoding nucleic acid of the present invention "stacked" in any desired combination with additional transgenic traits.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 18. Comparison of a portion of the wild type DMO polypeptide sequence with conserved regions of other iron-sulfur oxygenases showing that DMO is unique, with low identity to known enzymes, but WI 12 (arrow) is conserved in other iron-sulfur oxygenases and is bounded by two conserved domains, Rieske and Non-Haem Fe (SEQ ID NOS: 4-23).

DETAILED DESCRIPTION OF THE INVENTION

Figure 1:
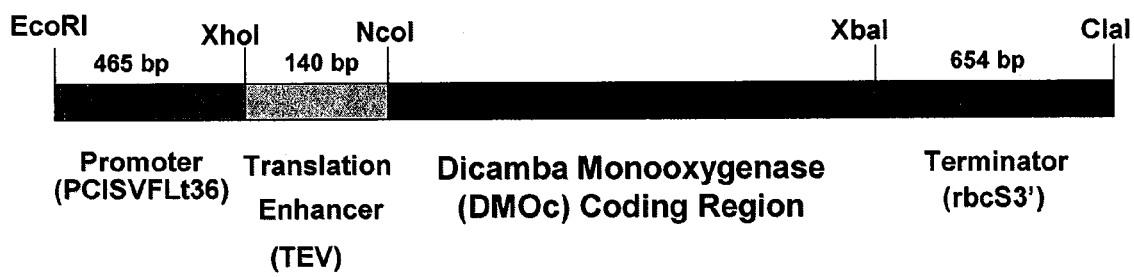
FIG. 1. Outline of the cassette used for genetic engineering of the dicamba monooxygenase gene (DMOc) for expression in higher plants using the FLt36 promoter from peanut chlorotic streak virus, the tobacco etch virus (TEV leader) translation enhancer sequence, and a terminator region from the pea Rubisco small subunit gene. Another genetically engineered version of the DMOc gene that was prepared contained a transit peptide coding region from the pea Rubisco small subunit gene for chloroplast localization of DMO between the TEV translation enhancer region and the coding region for DMOc.

The invention provides dicamba monooxygenase (DMO) variants comprising a cysteine at a position corresponding to position 112 of the DMO shown in SEQ ID NO:1, designated herein DMOc. It was demonstrated that DMOc yields high level tolerance to the herbicide dicamba when expressed in transgenic plants. The results were surprising as the altered amino acid position is highly conserved in other iron-sulfur oxygenases. Of 78 iron-sulfur oxygenase sequences analyzed from 45 species, all of the 52 oxygenase sequences with at least 15% identity had a W corresponding to the position at amino acid 112 of SEQ ID NO:1, despite a highest total identity of only 38%. This position is also bounded by two conserved functional domains (FIG. 18). The high level herbicide tolerance DMOc yielded was thus unexpected.

Analysis of the Michaelis-Menten parameters for DMOc relative to the unaltered sequence (DMOw; U.S. Pat. No. 7,022,896) revealed that the enzymes were different in terms of catalytic efficiencies: DMOc was five times more efficient than DMOw and DMOc appeared to have a higher turnover number and tighter substrate binding. In addition, DMOc functioned better at lower pH conditions and higher temperature relative to the native enzyme. These results indicated the potential for selecting DMO variants for use in a particular transgenic plant based on expected conditions of use, such as crop growing conditions. One aspect of the invention therefore involves identifying a candidate crop growing environment for at least a first crop species, and identifying a DMO enzyme most suited to that environment based on the kinetics, for example of DMOc and DMOw. For example, one of skill in the art may, in particular embodiments, select a DMOc coding sequence for use in plants presenting lower pH conditions in planta and/or in the case of growing environments with higher temperatures relative to other plant species or growing environments, respectively. Dicamba can be applied by incorporation in soil (preplant incorporation); spraying the soil (pre-emergence); and over the top of plants (post-emergence treatment), while levels of tolerance to dicamba may differ at various times during plant growth.

As indicated above, tolerance to extremely high levels of the herbicide dicamba was obtained in transgenic plants expressing DMOc. In tobacco, for example, which is normally sensitive to even very low levels of dicamba, transgenic plants were created expressing DMOc that were tolerant to dicamba treatment at 5.6 kg/ha or higher, e.g., 10-20 fold greater than normally recommended field application rates for control of broadleaf weeds. When the DMOc gene was inserted into the chloroplast genome of tobacco plants, dicamba tolerance to at least 28 kg/ha was obtained. Transgenic soybeans, tomato and *Arabidopsis thaliana* plants bearing a nuclear-encoded DMOc gene were also created and found tolerant to high levels of dicamba. For example, insertion of DMOc into the nuclear genome of soybean plants yielded tolerance to treatments of 2.8 kg/ha, thus permitting use of dicamba to control weeds in fields of DMOc expressing plants.

DMOc was thus demonstrated to be effective in conferring dicamba tolerance without the need for additional coding sequences such as *P. maltophilia*, strain DI-6, ferredoxin or reductase. The modified DMO gene was inherited stably as a Mendelian gene with no apparent loss of penetrance or expression. While somewhat stronger expression was obtained with a chloroplast transit peptide, transgenic plants with a DMO transgene lacking the transit peptide coding sequence also exhibited high level post-emergence dicamba tolerance.

A. Nucleic Acids and Recombinant Constructs

1. Dicamba Monooxygenase (DMO)

In one embodiment of the present invention, DNA constructs are provided comprising a nucleic acid encoding a dicamba monooxygenase polypeptide comprising a cysteine at a position corresponding to position 112 of SEQ ID NO:1. An exemplary DMO coding sequence is provided herein as SEQ ID NO:2. This sequence, in addition to comprising cysteine at position of 112 of SEQ ID NO:1, included the addition of a GCC codon (alanine) following the ATG start codon to add a Nco I restriction site relative to the native coding sequence and to facilitate cloning. The polypeptide in SEQ ID NO:1 therefore also included an additional Ala residue immediately following the Met encoded by the start codon. The transit peptide sequence was excised from the plasmid with Bgl II and EcoR I and then cloned into the BamH I and EcoR I sites of the pBluescript II KS+ vector. This construct was used as the template in a PCR reaction with primers that added Nco I restriction sites to either end of the transit peptide coding sequence. Digestion of the PCR product with Nco I allowed insertion of the transit peptide coding sequence into the ATG initiation codon site of the modified DMO gene.

Thus, in one embodiment of the invention, sequences encoding the polypeptide of SEQ ID NO:1, including, but not limited to, SEQ ID NO:2, are provided. As is well known in the art, homologous sequences and derivatives of these sequences may readily be prepared and used. For example, a nucleic acid may be used that encodes a DMO polypeptide having at least 90% sequence identity to the DMOc polypeptide of SEQ ID NO:1, including at least about 92%, 94%, 95%, 96%, 97%, 98%, 99% or greater identity to such sequences. A nucleic acid may also be used that exhibits at least 90% sequence identity to the nucleic acid sequence provided as SEQ ID NO:2, including at least about 92%, 94%, 95%, 96%, 97%, 98%, 99% or greater identity to such a sequence and which encodes a DMO comprising a cysteine at position 112. In one embodiment, sequence identity is determined using the Sequence Analysis software package of the GCG Wisconsin Package (Accelrys, San Diego, Calif.), MEGAlign (DNAStar, Inc., 1228 S. Park St., Madison, Wis. 53715) with default parameters. Such software matches similar sequences by assigning degrees of similarity or identity.

A polynucleotide molecule that expresses a DMO polypeptide can be obtained by techniques well known in the art in view of the current disclosure. Variants of DMOs provided herein having a capability to degrade dicamba can thus be prepared and assayed for activity according to the methodology disclosed herein. Such sequences can also be identified, for example, from suitable organisms including bacteria that degrade dicamba (U.S. Pat. No. 5,445,962; Krueger et al., 1989; Cork and Krueger, 1991; Cork and Khalil, 1995). One means of isolating a cloned DMO sequence is by nucleic acid hybridization, for example, to a library constructed from the source organism, or by RT-PCR using mRNA from the source organism and primers based on the disclosed DMO. The invention therefore encompasses use of nucleic acids hybridizing under stringent conditions to a DMO encoding sequence described herein. One of skill in the art understands that conditions may be rendered less stringent by increasing salt concentration and decreasing temperature. Thus, hybridization conditions can be readily manipulated, and thus will generally be a method of choice depending on the desired results. An example of high stringency conditions is 5×SSC, 50% formamide and 42° C. By conducting a wash under such conditions, for example, for 10 minutes, those sequences not hybridizing to a particular target sequence under these conditions can be removed. One embodiment of the invention thus comprises use of a DMO-encoding nucleic acid that is defined as hybridizing under wash conditions of 5×SSC, 50% formamide and 42° C. for 10 minutes to a nucleic acid according to SEQ ID NO:2.

Variants can also be chemically synthesized using the DMO polynucleotide sequences described herein according to techniques well known in the art. For instance, DNA sequences may be synthesized by phosphoamidite chemistry in an automated DNA synthesizer. Chemical synthesis has a number of advantages. In particular, chemical synthesis is desirable because codons preferred by the host in which the DNA sequence will be expressed may be used to optimize expression. An example of such a sequence that was optimized for expression in dicots using *Arabidopsis thaliana* codon usage is the DMO sequence shown in SEQ ID NO:3. The polypeptide, predicted to have an Ala, Thr, Cys at positions 2, 3, 112, respectively, is given in SEQ ID NO:1. The Ala residue at position 2 was added relative to the wild type DMO as a result of the addition of a codon for alanine immediately following the ATG initiation codon to simplify vector construction, as explained below.

Not all of the codons need to be altered to obtain improved expression, but preferably at least the codons rarely used in the host are changed to host-preferred codons, e.g., codons more frequently used in the host and which generally are more readily translated than rare, non-preferred codons. High levels of expression can be obtained by changing greater than about 50%, most preferably at least about 80%, of non-preferred codons to host-preferred codons. The codon preferences of many host cells are known (PCT WO 97/31115; PCT WO 97/11086; EP 646643; EP 553494; and U.S. Pat. Nos. 5,689,052; 5,567,862; 5,567,600; 5,552,299 and 5,017,692). The codon preferences of other host cells can be deduced by methods known in the art. Also, using chemical synthesis, the sequence of the DNA molecule or its encoded protein can be readily changed to, for example, optimize expression (for example, eliminate mRNA secondary structures that interfere with transcription or translation), add unique restriction sites at convenient points, and delete protease cleavage sites.

Modification and changes may be made to the polypeptide sequence of a protein such as the DMO sequences provided herein while retaining enzymatic activity. The following is a discussion based upon changing the amino acids of a protein to create an equivalent, or even an improved, modified polypeptide and corresponding coding sequences. In particular embodiments of the invention, DMO sequences may be altered in this manner and used in the methods of the invention. The amino acid changes may be achieved by changing the codons of the DNA sequence.

It is known, for example, that certain amino acids may be substituted for other amino acids in a protein structure without appreciable loss of interactive binding capacity with structures such as binding sites on substrate molecules. Since it is the interactive capacity and nature of a protein that defines that protein's biological functional activity, certain amino acid sequence substitutions can be made in a protein sequence, and, of course, the underlying DNA coding sequence, and nevertheless obtain a protein with like properties. It is thus contemplated that various changes may be made in the DMO peptide sequences described herein and corresponding DNA coding sequences without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte et al., 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. Here, the observation that a DMO having a substitution of a tryptophan at position 112 with cysteine had biological activity and resulted in plants tolerant to high levels of dicamba was surprising given the different hydropathic indices between the native and altered amino acids and thus would not be used by those skilled in the art for creating functional variants according to the prior art.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those which are within ±1 are particularly preferred, and those within ±0.5 are even more particularly preferred. Exemplary substitutions which take these and various of the foregoing characteristics into consideration are well known to those of skill in the art and include: arginine and lysine; glutamate and aspartate; serine and threonine; glutamine and asparagine; and valine, leucine and isoleucine. Again, the activity of DMOc was surprising given the very different hydrophilic values between the altered and native amino acids and this substitution would not be used by those skilled in the art for creating functional variants according to the prior art.

The modification of a DMO sequence according to the invention can be guided by consideration of the conserved domains within the enzyme. For example, it is demonstrated below that the DMO enzyme contains functional domains such as a Rieske iron-sulfur cluster and a binding site for free iron (see FIG. 18, for example). This information combined with knowledge in the art regarding the functional domains and modification of proteins generally can therefore be used to generate modified DMO enzymes while maintaining enzymatic activity within the scope of the invention (see, e.g., Mason and Cammack, 1992; Jiang et al., 1996).

2. Transformation Constructs

A DMO-encoding polynucleotide used in accordance with the invention will typically be introduced into a cell as a construct comprising expression control elements necessary for efficient expression. Methods of operatively linking expression control elements to coding sequences are well known in the art (Maniatis et al., 1982; Sambrook et al., 1989). Expression control sequences are DNA sequences involved in any way in the control of transcription. Suitable expression control sequences and methods of using them are well known in the art. A promoter in particular may be used, with or without enhancer elements, 5' untranslated region, transit or signal peptides for targeting of a protein or RNA product to a plant organelle, particularly to a chloroplast and 3' untranslated regions such as polyadenylation sites. One skilled in the art will know that various enhancers, promoters, introns, transit peptides, targeting signal sequences, and 5' and 3' untranslated regions (UTRs) are useful in the design of effective plant expression vectors, such as those disclosed, for example, in U.S. Patent Application Publication 2003/01403641.

Promoters suitable for the current and other uses are well known in the art. Examples describing such promoters include U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the cauliimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987), the sucrose synthase promoter (Yang et al., 1990), the R gene complex promoter (Chandler et al., 1989), and the chlorophyll a/b binding protein gene promoter, etc. Particularly beneficial for use with the present invention may be CaMV35S (U.S. Pat. Nos. 5,322,938; 5,352,605; 5,359,142; and 5,530,196), FMV35S (U.S. Pat. Nos. 6,051,753; 5,378,619), a PClSV promoter (e.g. U.S. Pat. No. 5,850,019, and SEQ ID NO:24), and AGRtu.nos (GenBank Accession V00087; Depicker et al, 1982; Bevan et al., 1983) promoters.

Benefit may be obtained for the expression of heterologous genes by use of a sequence coding for a transit peptide. Transit peptides generally refer to peptide molecules that when linked to a protein of interest directs the protein to a particular tissue, cell, subcellular location, or cell organelle. Examples include, but are not limited to, chloroplast transit peptides, nuclear targeting signals, and vacuolar signals. A chloroplast transit peptide is of particular utility in the present invention for directing expression of a DMO enzyme to the chloroplasts. It is anticipated that DMO function will be facilitated by endogenous reductases and ferredoxins found in plant cells to degrade dicamba. Plant chloroplasts are particularly rich in reductases and ferredoxins. Accordingly, in a preferred embodiment for the production of transgenic dicamba-tolerant plants a sequence coding for a peptide may be used that will direct dicamba-degrading oxygenase into chloroplasts. Alternatively or in addition, heterologous reductase and/or ferredoxin can also be expressed in a cell.

DNA coding for a chloroplast targeting sequence may preferably be placed upstream (5') of a sequence coding for DMO, but may also be placed downstream (3') of the coding sequence, or both upstream and downstream of the coding sequence. A chloroplast transit peptide (CTP) in particular can be engineered to be fused to the N-terminus of proteins that are to be targeted into the plant chloroplast. Many chloroplast-localized proteins are expressed from nuclear genes as precursors and are targeted to the chloroplast by a CTP that is removed during the import steps. Examples of chloroplast proteins include the small subunit (RbcS2) of ribulose-1,5,-bisphosphate carboxylase, ferredoxin, ferredoxin oxidoreductase, the light-harvesting complex protein I and protein II, and thioredoxin F. It has been demonstrated in vivo and in vitro that non-chloroplast proteins may be targeted to the chloroplast by use of protein fusions with a CTP and that a CTP is sufficient to target a protein to the chloroplast. For example, incorporation of a suitable chloroplast transit peptide, such as, the *Arabidopsis thaliana* EPSPS CTP (Klee et al., 1987), and the *Petunia hybrida* EPSPS CTP (della-Cioppa et al., 1986) has been shown to target heterologous EPSPS protein sequences to chloroplasts in transgenic plants. Other exemplary chloroplast targeting sequences include the maize cab-m7 signal sequence (Becker et al., 1992; PCT WO 97/41228) and the pea glutathione reductase signal sequence (Creissen et al., 1991; PCT WO 97/41228). In the present invention, AtRbcS4 (CTP1; U.S. Pat. No. 5,728,925), AtShkG (CTP2; Klee et al., 1987), AtShkGZm (CTP2synthetic; see SEQ ID NO:14 of WO04009761), and PsRbcS (Coruzzi et al., 1984) may be of particular benefit, for instance with regard to expression of a DMO polypeptide.

A 5' UTR that functions as a translation leader sequence is a DNA genetic element located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, plant rubisco leaders, among others (Turner and Foster, 1995). In the present invention, 5' UTRs that may in particular find benefit are GmHsp (U.S. Pat. No. 5,659,122), PhDnaK (U.S. Pat. No. 5,362,865), AtAntl, TEV (Carrington and Freed, 1990), and AGRtunos (GenBank Accession V00087; Bevan et al., 1983).

The 3' non-translated sequence, 3' transcription termination region, or poly adenylation region means a DNA molecule linked to and located downstream of the coding region of a gene and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. An example of a 3' transcription termination region is the nopaline synthase 3' region (nos 3'; Fraley et al., 1983). The use of different 3' nontranslated regions has been described (Ingelbrecht et al., 1989). Polyadenylation molecules from a *Pisum sativum* RbcS2 gene (Ps.RbcS2-E9; Coruzzi et al., 1984) and AGRtu.nos (Rojiyaa et al., 1987, Genbank Accession E01312) in particular may be of benefit for use with the invention.

A DMO-encoding polynucleotide molecule expression unit can be linked to a second polynucleotide molecule in an expression unit containing genetic elements for a screenable/scorable marker or for a gene conferring a desired trait. Commonly used genes for screening presumptively transformed cells include β-glucuronidase (GUS), β-galactosidase, luciferase, and chloramphenicol acetyltransferase (Jefferson, 1987; Teeri et al., 1989; Koncz et al., 1987; De Block et al., 1984), green fluorescent protein (GFP) (Chalfie et al., 1994; Haseloff et al., 1995; and PCT application WO 97/41228).

The second polynucleotide molecule may include, but is not limited to, a gene that acts as a selectable marker. A second or further gene may provide a desirable characteristic associated with plant morphology, physiology, growth and development, yield, nutritional enhancement, disease or pest resistance, or environmental or chemical tolerance and may include genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686,452; 6,657,046; 6,645,497; 6,642,030; 6,639,054; 6,620,988; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 5,959,091; 5,942,664; 5,942,658, 5,880,275; 5,763,245; 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013,864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. Nos. RE37,543; 6,228,623; 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes may be used with the invention as will be appreciated by those of skill in the art in view of the instant disclosure.

An expression unit may be provided as T-DNAs between right border (RB) and left border (LB) regions of a first plasmid together with a second plasmid carrying T-DNA transfer and integration functions in *Agrobacterium*. The constructs may also contain plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404. However, other strains known to those skilled in the art of plant transformation can function in the present invention.

3. Preparation of Transgenic Cells

Transforming plant cells can be achieved by any of the techniques known in the art for introduction of transgenes into cells (see, for example, Miki et al., 1993). Examples of such methods are believed to include virtually any method by which DNA can be introduced into a cell. Methods that have been described include electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184. Through the application of techniques such as these, the cells of virtually any plant species may be stably transformed and selected according to the invention and these cells developed into transgenic plants.

The most widely utilized method for introducing an expression vector into plants is based on the natural transformation system of *Agrobacterium* (for example, Horsch et al., 1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant (for example, Kado, 1991). Descriptions of *Agrobacterium* vector systems and methods for *Agrobacterium*-mediated gene transfer are provided by numerous references, including Miki et al., supra, Moloney et al., 1989, and U.S. Pat. Nos. 4,940,838 and 5,464,763. Other bacteria such as

*Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector (Brothers et al, 2005).

B. Tissue Cultures and Plant Regeneration

Regenerating a transformed plant cell into a fertile plant can be achieved by first culturing an explant on a shooting medium and subsequently on a rooting medium. Sometime, an explant may be cultured on a callus medium before being transferred to a shooting medium. A variety of media and transfer requirements can be implemented and optimized for each plant system for plant transformation and recovery of transgenic plants. Consequently, such media and culture conditions can be modified or substituted with nutritionally equivalent components, or similar processes for selection and recovery of transgenic events.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture. Some cell types will grow and divide either in liquid suspension or on solid media or on both media.

Recipient cell targets include, but are not limited to, meristem cells, callus, immature embryos and gametic cells such as microspores pollen, sperm and egg cells. Any cell from which a fertile transgenic plant may be regenerated may be used in certain embodiments. For example, immature embryos may be transformed followed by selection and initiation of callus and subsequent regeneration of fertile transgenic plants. Direct transformation of immature embryos obviates the need for long term development of recipient cell cultures. Meristematic cells (i.e., plant cells capable of continual cell division and characterized by an undifferentiated cytological appearance, normally found at growing points or tissues in plants such as root tips, stem apices, lateral buds, etc.) may also be used as a recipient plant cell. Because of their undifferentiated growth and capacity for organ differentiation and totipotency, a whole transformed plant could be recovered from a single transformed meristematic cell.

Somatic cells are of various types. Embryogenic cells are one example of somatic cells which may be induced to regenerate a plant through embryo formation. Non-embryogenic cells are those which typically will not respond in such a fashion.

Certain techniques may be used that enrich recipient cells within a cell population. For example, Type II callus development, followed by manual selection and culture of friable, embryogenic tissue, generally results in an enrichment of recipient cells for use in, for example, micro-projectile transformation.

In certain embodiments, recipient cells are selected following growth in culture. Cultured cells may be grown either on solid supports or in the form of liquid suspensions. In either instance, nutrients may be provided to the cells in the form of media, and environmental conditions controlled. There are many types of tissue culture media comprised of amino acids, salts, sugars, growth regulators and vitamins. Most of the media employed in the practice of the invention will have some similar components, while the media can differ in composition and proportions of ingredients according to known tissue culture practices. For example, various cell types usually grow in more than one type of media, but will exhibit different growth rates and different morphologies, depending on the growth media. In some media, cells survive but do not divide. Media composition is also frequently optimized based on the species or cell type selected.

Various types of media suitable for culture of plant cells have been previously described. Examples of these media include, but are not limited to, the N6 medium described by Chu et al. (1975) and MS media (Murashige & Skoog, 1962). In some embodiments, it may be preferable to use a media with a somewhat lower ammonia/nitrate ratio such as N6 to promote generation of recipient cells by maintaining cells in a proembryonic state capable of sustained divisions. Woody Plant Medium (WPM) can also be used (Lloyd and McCown, 1981).

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all factors in maintaining callus and/or suspension cultures that are useful as sources of recipient cells. Alternating callus between different culture conditions may be beneficial in enriching for recipient cells within a culture. For example, cells may be cultured in suspension culture, but transferred to solid medium at regular intervals. After a period of growth on solid medium, cells can be manually selected for return to liquid culture medium. Repeating this sequence of transfers to fresh culture medium may be used to enrich for recipient cells. Passing cell cultures through a 1.9 mm sieve may also be useful to maintain the friability of a callus or suspension culture and enriching for transformable cells when such cell types are used.

C. Transgenic Plants

Once a transgenic cell has been selected, the cell can be regenerated into a fertile transgenic plant using techniques well known in the art. The transformed plants can be subsequently analyzed to determine the presence or absence of a particular nucleic acid of interest in a DNA construct. Molecular analyses can include, but are not limited to, Southern blots (Southern, 1975) or PCR analyses, immunodiagnostic approaches. Field evaluations can also be used. These and other well known methods can be performed to confirm the stability of the transformed plants produced by the methods disclosed. These methods are well known to those of skill in the art (Sambrook et al., 1989).

Transgenic plants comprising a DMO coding sequence provided herein can thus be produced. In particular, economically important plants, including crops, trees, and other plants can be transformed with DNA constructs of the present invention so that they are dicamba tolerant or have increased tolerance. Plants that are currently considered tolerant to auxin-like herbicides thus can be transformed to increase their tolerance to the herbicide. Some non-limiting examples of plants that may find use with the invention include alfalfa, barley, beans, beet, broccoli, cabbage, carrot, canola, cauliflower, celery, Chinese cabbage, corn, cotton, cucumber, eggplant, leek, lettuce, melon, oat, onion, pea, pepper, peanut, potato, pumpkin, radish, rice, sweet corn, sorghum, soybean, spinach, squash, sugarbeet, sunflower, tomato, watermelon, and wheat.

Once a transgenic plant containing a transgene has been prepared, that transgene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct prepared in accordance with the invention. A "transgenic plant" may thus be of any generation. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the first plant bearing the fertilized flower.

The invention thus provides transgenic plant tissues comprising a DMO-encoding nucleic acid provided herein. The tissues may have been directly transformed with a DMO-encoding nucleic acid or inherited the nucleic acid from a progenitor cell. Tissues provided by the invention specifically include, but are not limited to, cells, embryos, immature embryos, meristematic cells, immature tassels, microspores, pollen, leaves, anthers, roots, root tips, flowers and seeds. Any such tissues, including any plant part, comprising a nucleic acid described herein, are thus provided by the invention. Seeds in particular will find particular benefit for use, both for commercial or food uses in the form of grain, as well as for planting to grow additional crops.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Vector Construction for Genetically Engineered DMO Gene

The DMOc variant coding sequence was initially generated by PCR amplification from a DMOw template. In this amplification, the coding region of DMOw was amplified from the plasmid pPLH1, which contained the DMOw gene as a 3.5 kbp Xho I/Sst I fragment of *P. maltophilia*, strain DI-6, DNA. For DNA amplification, a 5' primer was employed that inserted a Nco I restriction site near the 5' end of the PCR product and a codon for alanine immediately following the ATG initiation codon and a 3' primer that created an Xba I restriction site at the 3' end of the PCR product (procedural details provided below). The 112W to 112C change was subsequently identified by nucleic acid sequencing.

Figure 5:
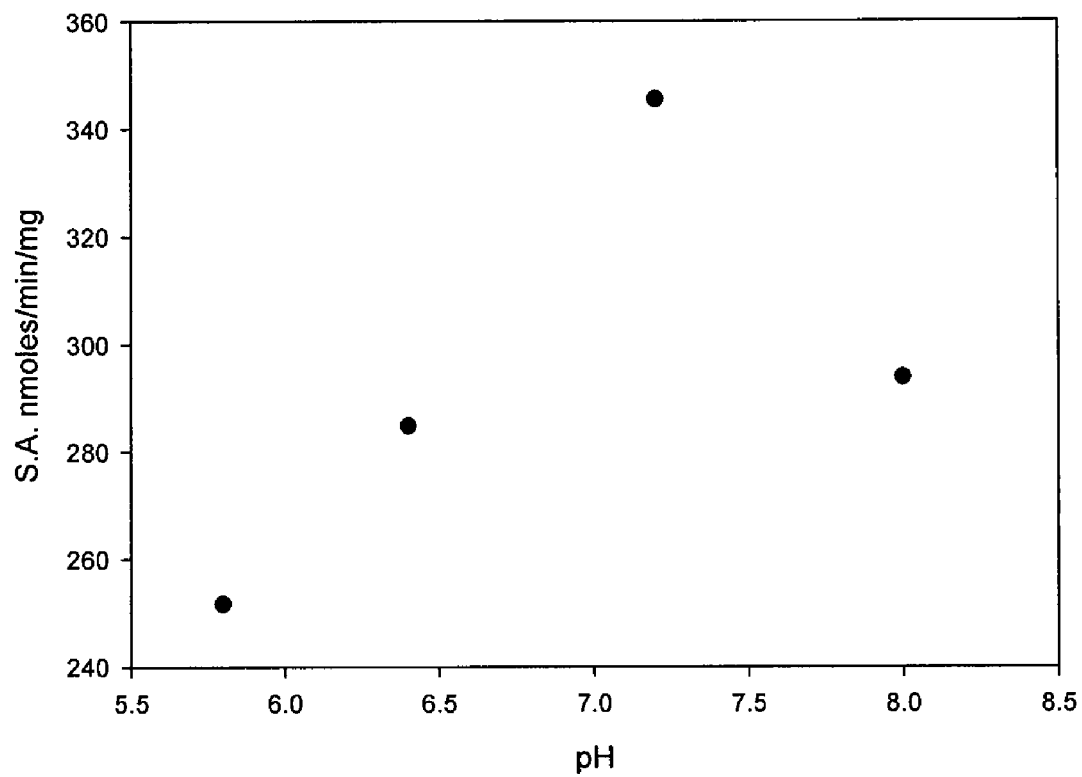
FIG. 5. Determination of optimum assay pH for DMOw.

For creation of the plant transformation vector, the DMOc gene was inserted using Nco I and Xba I sites added to the 5' and 3' ends, respectively, of the coding region into the pRTL2 vector (Carrington and Freed, 1990) thereby fusing the coding region to the vector's tobacco etch virus (TEV leader) translation enhancer element. The 5' Nco I site was introduced along with the addition of a GCC codon (alanine) following the ATG start codon and an Xba I restriction site was created at the 3' end of the codon region using specifically-designed PCR primers. To allow delivery of DMOc to the chloroplast, the chloroplast transit peptide coding region from the pea Rubisco subunit gene (Coruzzi et al., 1983) was placed upstream of the DMO coding region to allow targeting to the chloroplast. The transit peptide coding sequence carried on a Bgl II and EcoR I fragment was cloned into the BamH I and EcoR I sites of the pBluescript II KS+ vector. This construct was used as the template in a PCR reaction that inserted an Nco I site at both the 3' and the 5' ends of the transit peptide sequence. The amplified product was cloned into the Nco I site of the pRLT2 vector so that the transit peptide sequence was directly upstream and in frame with the coding region of the DMO gene. A cassette consisting of the TEV leader, transit peptide region and DMO DNA coding sequences was excised from the pRTL2 vector with Xho I and Xba I and cloned into the pKLP36 vector (U.S. Pat. No. 5,850,019; FIG. 5) using the same restriction sites for linking the cassette to a PClSV promoter and PsRbcS2-E9 poly A sequence. The new vector was labeled as pKLP36-TEV-TP-DMOc (also designated pKLP36-DMOc), and was deposited with the American Type Culture Collection (ATCC), 10801 University Boulevard, Manassas, Va. 20110-2209 USA on Feb. 2, 2006, and assigned ATCC Accession No. PTA-7357.

The pKLP36-DMOc vector was used for transforming tobacco, *Arabidopsis* and tomato plants. For soybean transformation, the DMOc cassette was cut out of the pKLP36-TEV-TP-DMOc as a EcoR I/Acc I segment and cloned into EcoR I/Acc I digested pPZP101 (Hajdukiewicz et al., 1994) for obtaining right and left borders. This vector (pPZP101+DMOc cassette) was then cut with ScaI and the DMOc cassette was cloned into the binary vector pPTN200 (see below), a derivative of pPZP201 (Hajdukiewicz et al., 1994), that contains a bar cassette flanked by left and right T-DNA borders and allows for selection of regenerating transformants in the presence of the herbicide Basta. The new two T-DNA binary vector was designated pPTN348 and used for soybean transformation. The vector pPTN200 was prepared by first cloning a nos promoter-bar element from pGPTV-bar (Becker et al., 1992) as a PstI/BamHI segment into pPZP201 (see Hajdukiewicz et al., 1994) and the resultant plasmid was named as pPTN193. The nos terminator from pE7113-GUS (see Mitsuhara et al., 1996) was cloned into pPTN193 downstream of the nos promoter-bar element to obtain the bar cassette.

Restriction and other enzymes were obtained from either Fermentas or Invitrogen. DIG-11-dUTP (alkali-labeled), CSPD (ready-to-use), DIG III molecular weight markers, anti-digoxigenin-AP (Fab fragments) and blocking reagent were obtained from Roche. Prehybridization solution, ULTRAhyb, was obtained from Ambion. DIG-RNA molecular weight marker I was obtained from Roche. Anti-rabbit IgG, peroxidase-linked antibody (donkey) and Hybond ECL (nitrocelluose) membrane were obtained from Amersham Biosciences. DNA, RNA and Protein blots, recombinant DNA techniques, and other molecular biology procedures were carried out using standard techniques (Ausubel et al., 1995).

Example 2

Production and Analysis of Transgenic Plants

Tobacco, tomato, soybeans and *Arabidopsis* were used for transgenic expression of the genetically engineered DMOc gene and confirmation of dicamba tolerance in plants expressing the gene. The DMOc coding sequence in binary vector pKLP36 was introduced into *A. tumefaciens* strain C58C1 containing the disarmed Ti plasmid pMP90 (Koncz and Schell, 1986) by triparental mating (Ditta 1980). The resultant transconjugants were used for tobacco (cv Xanthi) and tomato (cv Rutgers) transformation using the leaf disc protocol described by Horsch et al. (Horsch 1985). *Arabidopsis thaliana* was transformed by the floral dip technique (Clough and Bent, 1998). Transformation of soybean varieties Thorne and NE-3001 was carried out by cotyledonary-node *Agrobacterium*-mediated transformation system (Zhang et al., 1999).

Figure 2:
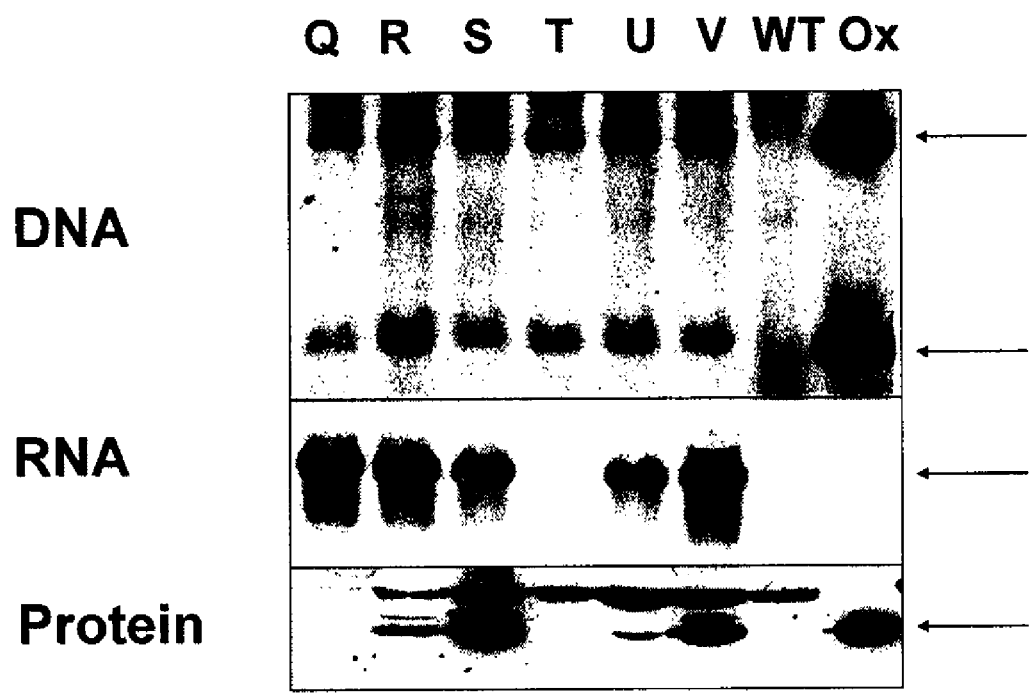
FIG. 2. DNA, RNA and protein blots panels demonstrating the presence and expression of the genetically engineered DMO gene in $T_1$ generation transgenic tobacco plants. Lanes Q through V depict DNA, mRNA and DMO species extracted from various $T_1$ generation transgenic tobacco plants. Extracts from a nontransgenic tobacco plant are depicted in lane WT while lane Ox exhibits a restriction-digested product of the cloned DMO gene construct (top panel) and the ~37 kDa DMO enzyme overproduced in *E. coli* (bottom panel). The ~55 kDa large subunit of Rubisco was detected in the protein blot by adding Rubisco antibodies to the DMO antisera and the detection of Rubisco served as an internal standard for comparing total protein loads in each lane. Equal amounts of RNA were loaded in each lane as judged by ethidium bromide staining of a duplicate gel. The arrows indicate the location of the DMO DNA, mRNA, or protein band.

*Agrobacterium*-mediated gene transfer of the DMOc gene to the nuclear genome of tobacco plants yielded several independently derived $T_1$ generation plants. The plants were tested for the presence and expression of the DMOc gene using DNA, RNA and protein blot analyses. FIG. 2 illustrates that, although all transgenic plants (lanes 1-6) in this analysis contained the same DNA fragments after restriction enzyme digestion as the cloned DMO gene (lane 8), the level of mRNA transcripts and DMO protein varied significantly between transformants. For example, the plant whose extracts are depicted in lane 5 shows relatively high levels of DMO mRNA but very low levels of the enzyme. Conversely, nearly equal levels of DMO mRNA in extracts shown in lane 3 were coupled with high-level expression of DMO. However, it was shown that events with strong expression could be consistently obtained by this method.

Plants in the greenhouse were sprayed with solvent and commercial grade dicamba (Clarity; BASF) using a compressed air, motor-driven, track sprayer with a flat-fan 8002E nozzle traveling at 1.87 mph. Additives included; 28% urea ammonium nitrate at 1.25% v/v and nonionic surfactant at 1.0% v/v. The solution containing dicamba at various concentrations was applied at 182 L/ha (40 gallons per acre). Soybean field plantings were sprayed with Clarity herbicide at 2.8 kg/ha (2.5 lb/ac).

Tobacco plants, like most dicotyledonous plants, are quite sensitive to treatment with dicamba. This was illustrated by comparison of nontransgenic tobacco plants untreated or treated with increasing amounts of dicamba. Herbicide damage symptoms were easily detected after spraying dicamba at a level of 0.017 kg/ha. Symptoms were quite severe at 0.28 kg/ha and 0.56 kg/ha, the levels normally used for weed control in agricultural applications.

Figure 3:
FIG. 3. Effect of treatment with dicamba at 2.2 kg/ha on two $T_1$ tobacco plants, one containing the genetically engineered DMOc gene lacking a chloroplast transit peptide coding sequence (right) and one lacking the DMOc gene (second from the right). The transgenic plant on the right displays little, if any, damage from dicamba treatment. The two plants to the left were not treated with dicamba and represent a nontransgenic plant (left) and a transgenic plant containing the DMOc gene (second from left).

Post-emergence treatment of DMOc-containing transgenic tobacco plants with 5.6 kg/ha (10 to 20 fold higher than normal application rates) caused few, if any symptoms while a nontransgenic plant suffered severe damage. Damage to the lower leaves of the transgenic plants could be duplicated by spraying plants with the surfactant-containing solvent solution used as the vehicle for dicamba application. Leaves produced after treatment of the transgenic plants with dicamba exhibited no visible signs of damage. Transgenic tomato plants carrying the genetically engineered DMOc gene, likewise, showed no damage when sprayed with high levels of dicamba, in this particular case, first with 0.56 kg/ha and subsequently with 5.6 kg/ha. *Arabidopsis thaliana* expressing the DMOc gene also displayed strong tolerance to treatment with dicamba. In this study, the concentration of dicamba employed provided a dose of 1.12 kg/ha. An unexpected finding was the observation that tobacco plants transformed with a DMOc gene lacking a transit peptide coding region were also tolerant to post-emergence treatments with dicamba at concentrations on average only slightly below that of plants bearing DMOc genes with transit peptide coding regions. In this study, treatments were compared using 2.2 kg/ha dicamba on two $T_1$ tobacco plants, one carrying DMOc lacking a chloroplast transit peptide and the other completely lacking the DMOc gene due to genetic segregation. The later plant was fully susceptible to damage caused by dicamba treatment and succumbed to the treatment (FIG. 3). The transgenic plant carrying the DMOc gene lacking the transit peptide was fully tolerant to treatment with dicamba at 2.2. kg/ha. Genetic studies of the inheritance of the DMOc gene in transgenic tobacco plants also demonstrated that the trait was inherited in most plants in a normal Mendelian fashion and maintained the original levels of expression in regard to herbicide tolerance.

In soybeans, over 50 $R_0$ transgenic soybean events were produced and $T_1$, $T_2$, and $T_3$ generation seeds collected. Because an *Agrobacterium tumefaciens* binary vector system was used, both transgenic plants bearing a marker gene and marker-free transgenic plants containing the DMOc gene were recovered. In either case, most transgenic soybean lines showed significant tolerance to treatment with dicamba at 2.8 kg/ha and 5.6 kg/ha under greenhouse conditions and strong tolerance to dicamba at 2.8 kg/ha (the highest level tested) in two years of field trials. These results suggest a broad margin of safety for transgenic soybeans and other crops carrying the DMOc gene coupled to highly effective control of a wide range of broadleaf weeds.

The high levels of dicamba-resistance in transgenic soybean plants bearing the DMO gene indicates the ability to apply dicamba in soybean fields to strongly suppress competition from broadleaf weeds without crop damage. In addition, dicamba-resistant crops can be an important complement to current weed control options using transgenic, herbicide-tolerant crops. That is, they can be a valuable asset in strategies to control presently existing herbicide-resistant weeds and to suppress the appearance of additional herbicide-resistant weeds that ultimately could threaten the long-term use and value of current herbicides and herbicide-tolerant crops.

Example 3

Overexpression, Purification and Comparison of DMOw and DMOc Enzymatic Properties A. Cloning and Overexpression The wild type (DMOw) and variant (DMOc) DMO coding sequences were cloned from plasmids pMON95900DMO (DMOw) and pMON58499DMO (DMOc) into vector pET28b (Novagen, San Diego, Calif.) and transformed into *Escherichia coli* BL21 cells (Novagen, San Diego, Calif.). Cells were grown in 1 liter of Luria-Bertani broth at 37° C. to an absorbance at 600 nm of 0.4 to 0.6. Protein expression was induced by adding 50 µM $Fe(NH_4)SO_4$, 100 µM $Na_2S$, and 1 mM isopropyl-beta-thiogalac-topyranoside (IPTG) and the cells were switched to 15° C. After 48-72 hours at 15° C., the cells were harvested by centrifugation at 10000×g for 20 minutes. For further usage the cells were stored at −20° C.

The yield of protein expression in E. coli for DMOw and DMOc was different. While the DMOw yield was about 100 to 150 mg of pure protein per liter of LB medium, the DMOc yield was 10 fold lower, or about 10 to 15 mg of pure protein per liter. This was not predicted as E. coli does not have rare codons for cysteine and there is only one codon for tryptophan, but the ability to produce the proteins heterologously in E. coli was shown in both cases regardless of yield. The amount of protein in inclusion bodies was low in both cases, suggesting that the protein primarily stays in the soluble fraction.

His-tagged recombinant DMOw protein from *Pseudomonas maltophilia*, strain DI-6 and His-tagged recombinant DMOc expressed in *E. coli* stain BL21, were purified to homogeneity by Ni-NTA column chromatography. Cells were suspended in Lysis buffer (100 mM NaPi pH 8.0, 300 mM NaCl, and 10 mM imidazole) and disrupted by sonication. The cell lysate was centrifuged at 55000×g for 1 hour. The supernatant was loaded on a Ni-NTA column, which was washed with Wash buffer (100 mM NaPi pH 8.0, 300 mM NaCl, and 20 mM imidazole) to remove proteins that are nonspecifically attached to the resin. The His-tagged protein was eluted with Elution buffer (100 mM NaPi pH 8.0, 300 mM NaCl, and 250 mM imidazole). For DMOw purification, a stepwise gradient was enough to obtain 95% pure enzyme, while for DMOc, a linear gradient from 20 to 250 mM concentration of imidazole was needed to achieve the same level of purity. The enzyme that was eluted from the column was approximately 95% pure as estimated by protein blots (western blots) of the enzyme after size-fractionation on SDS-polyacrylamid gel electrophoresis. A single major band migrating at approximately 40 kDa (37.3 kDa DMO enzyme plus 3 kDA for the His-tag), indicated that the correct protein had been overproduced.

B. Assay for DMOc and DMOw and Steady State Kinetics

Protein concentrations were determined by Bradford assay with rabbit IgG as standard. Proteins were separated by SDS-PAGE and stained with Coomassie Blue. DMO activity was measured by following the formation of DCSA which was separated by HPLC (Waters Corporation, Milford, Mass.) by using a Discovery C18 column (Supelco, Sigma-Aldrich, St. Louis, Mo.). The retention time for DCSA was 8 minutes and for dicamba was 9.5 minutes. For kinetic studies the DCSA was detected and quantified by fluorescence emission at 420 nm (excitation wavelength 310 nm) after separation on the HPLC column from reaction mixture. Set concentrations of DCSA (12 and 24 µM) were used as quantification standards.

Stock solution of dicamba (100, 200, 400, 800, 1000, 2000, 5000, and 10000 µM), 0.1 M KPi pH 7.2, 0.1 M FeSO$_4$, 0.1 M NADH, and 1 M MgCl$_2$ were used. The assays were performed at 30° C. for 20 minutes and the reaction was quenched by addition of 40 µl of H$_2$SO$_4$. For activity measurements DMO was coupled with an excess of purified ferredoxin and reductase from *P. maltophilia* strain DI-6.

Figure 4:
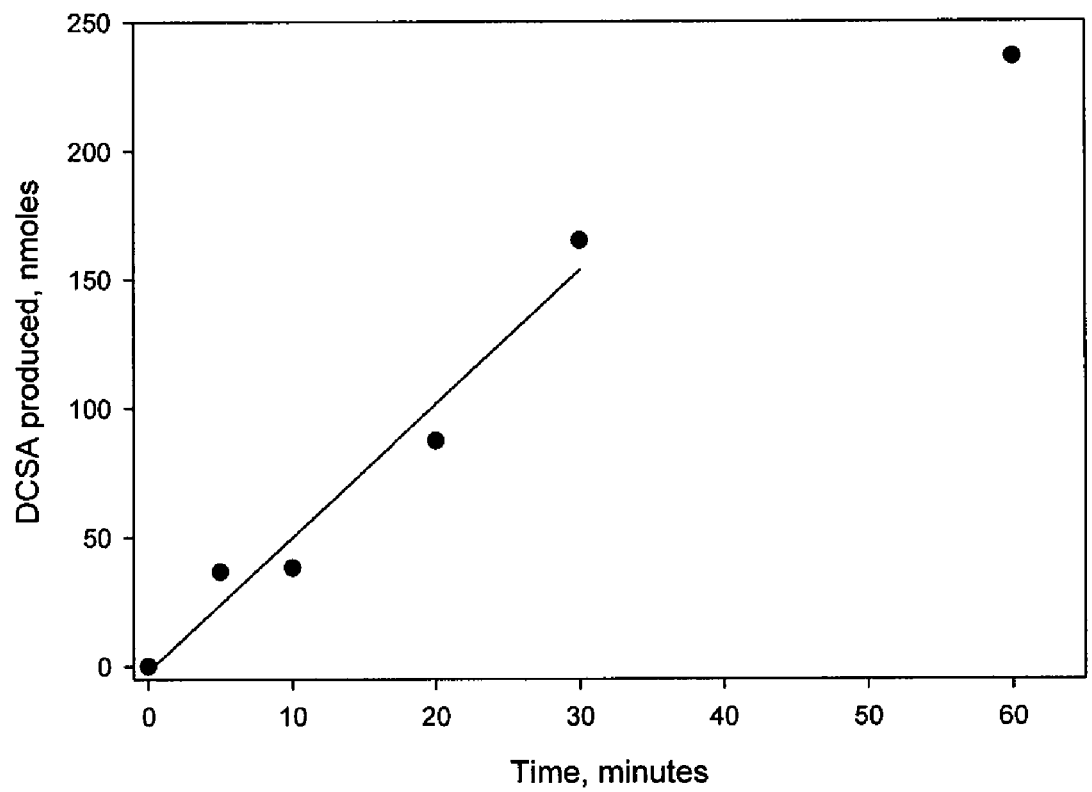
FIG. 4. Formation of DCSA vs. time by DMOw.
Figure 6:
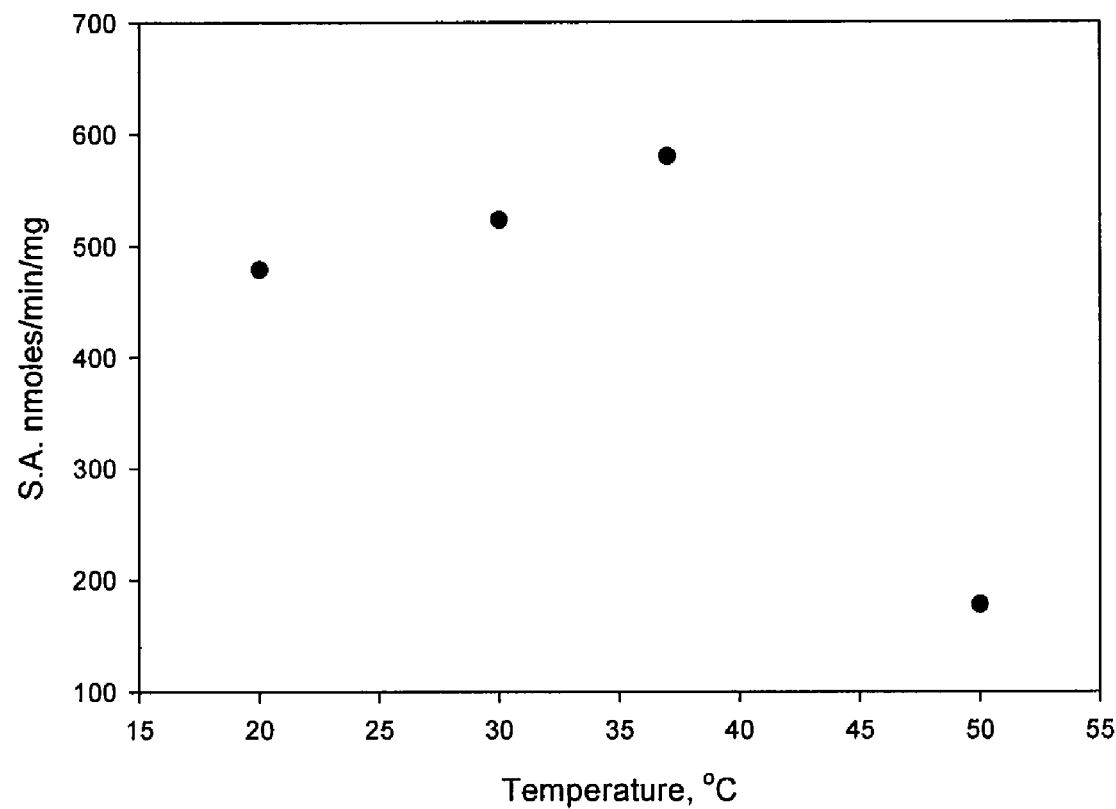
FIG. 6. Determination of optimum assay temperature for DMOw.

Since the assay for DMO activity was a discontinuous assay, it was important to establish the time for which the assay has to be run in order to obtain meaningful kinetic parameters. The assay thus has to be run under initial condition as the amount of DCSA produced is linear for the time the assay is being run (FIG. 4). The results suggested that the assay could be run between 20 to 30 minutes and still maintain linearity. FIG. 5 shows that the optimum pH for the assay performed in the presence of 0.1 M Kpi buffer was 7.2 and the optimum temperature was found to be approximately 37° C. (FIG. 6).

C. Analysis of Kinetic Data

The Michaelis-Menten parameters were determined by fitting the data to a nonlinear steady-state equation (Equation 1). The data were analyzed using Sigma plot 8.0 (Jandel Scientific).

$$V_o = V\text{max}*[S]/(Km+[S])$$  Equation 1

Figure 7:
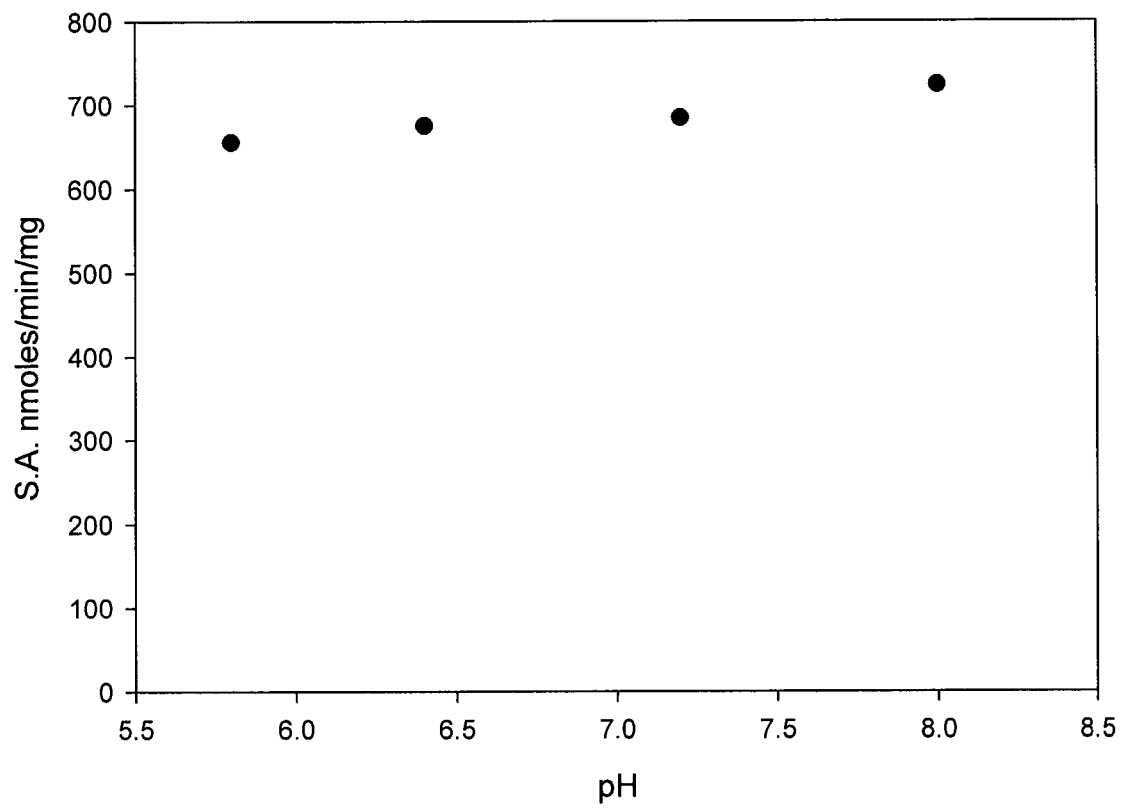
FIG. 7. Determination of optimum pH for DMOc.
Figure 8:
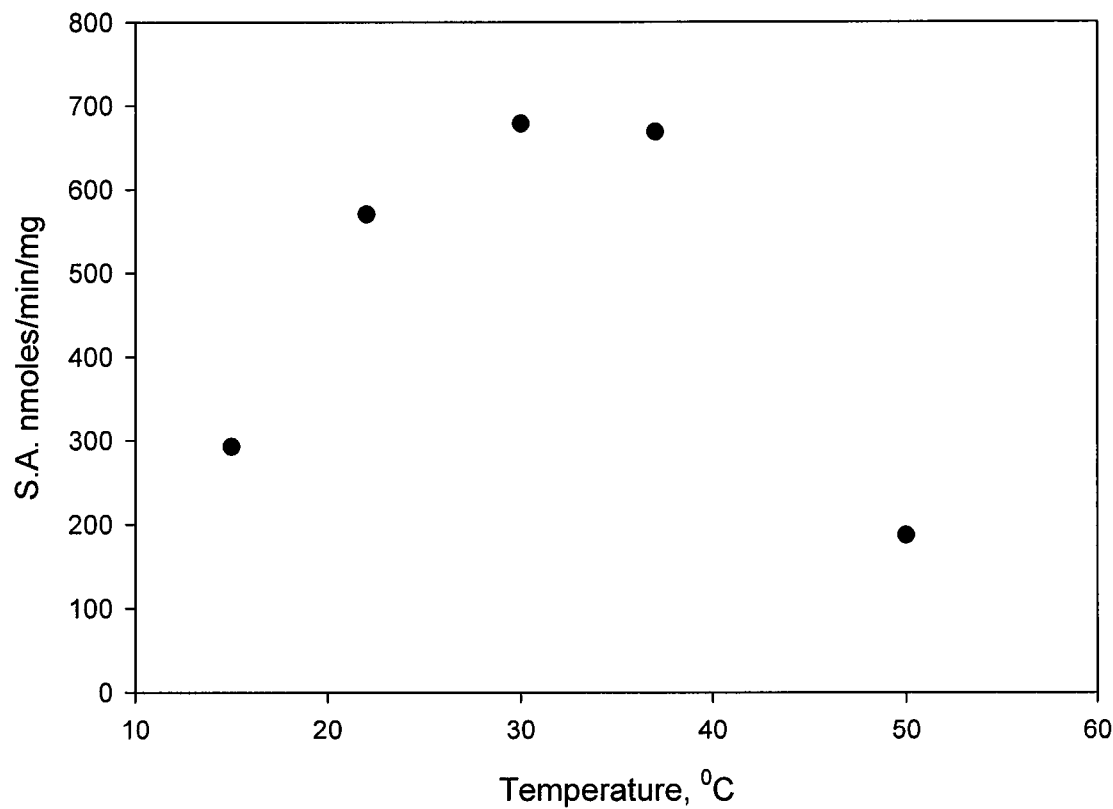
FIG. 8. Determination of optimum temperature for DMOc.

The optimum pH and temperature were also determined for DMOw and DMOc. Optimum pH was measured at 30° C. for 20 minutes and optimum temperature determination was measured also for 20 minutes at pH 7.2 for both forms of the enzyme. The results are summarized in FIGS. 7-9 and are discussed below.

Figure 10:
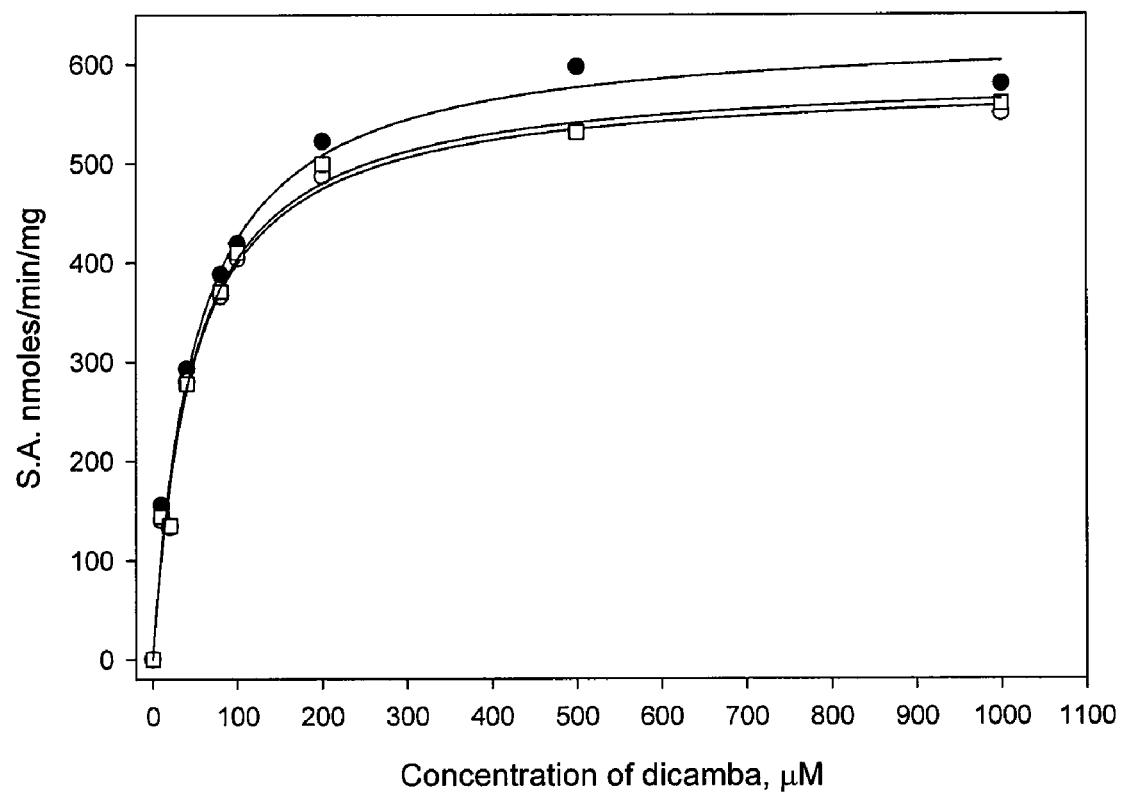
FIG. 10. Steady state kinetics for DMOw.
Figure 11:
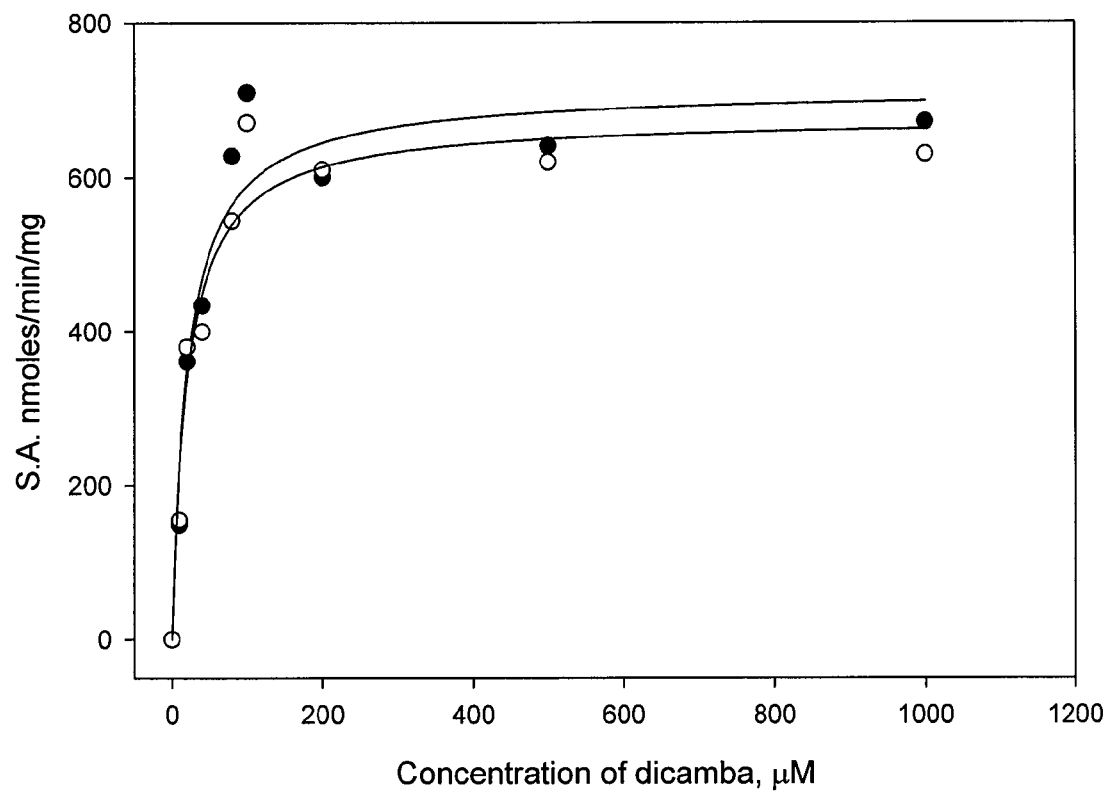
FIG. 11. Steady state kinetics for DMOc.

The studies show that DMOw and DMOc differ in kinetic properties. For example, the Michaelis-Menten parameters calculated for DMOw and DMOc are: for DMOw, Km=49±7 µM and Vmax=633±24 nmoles/min/mg, and for DMOc, Km=20.5±5 µM and Vmax=676±37 nmoles/min/mg. These results are shown in FIGS. 10 and 11 and are summarized in Table 1 below. In addition, two additional analyses carried out for DMOw and DMOc yielded similar results (Table 2 and 3).

Figure 9:
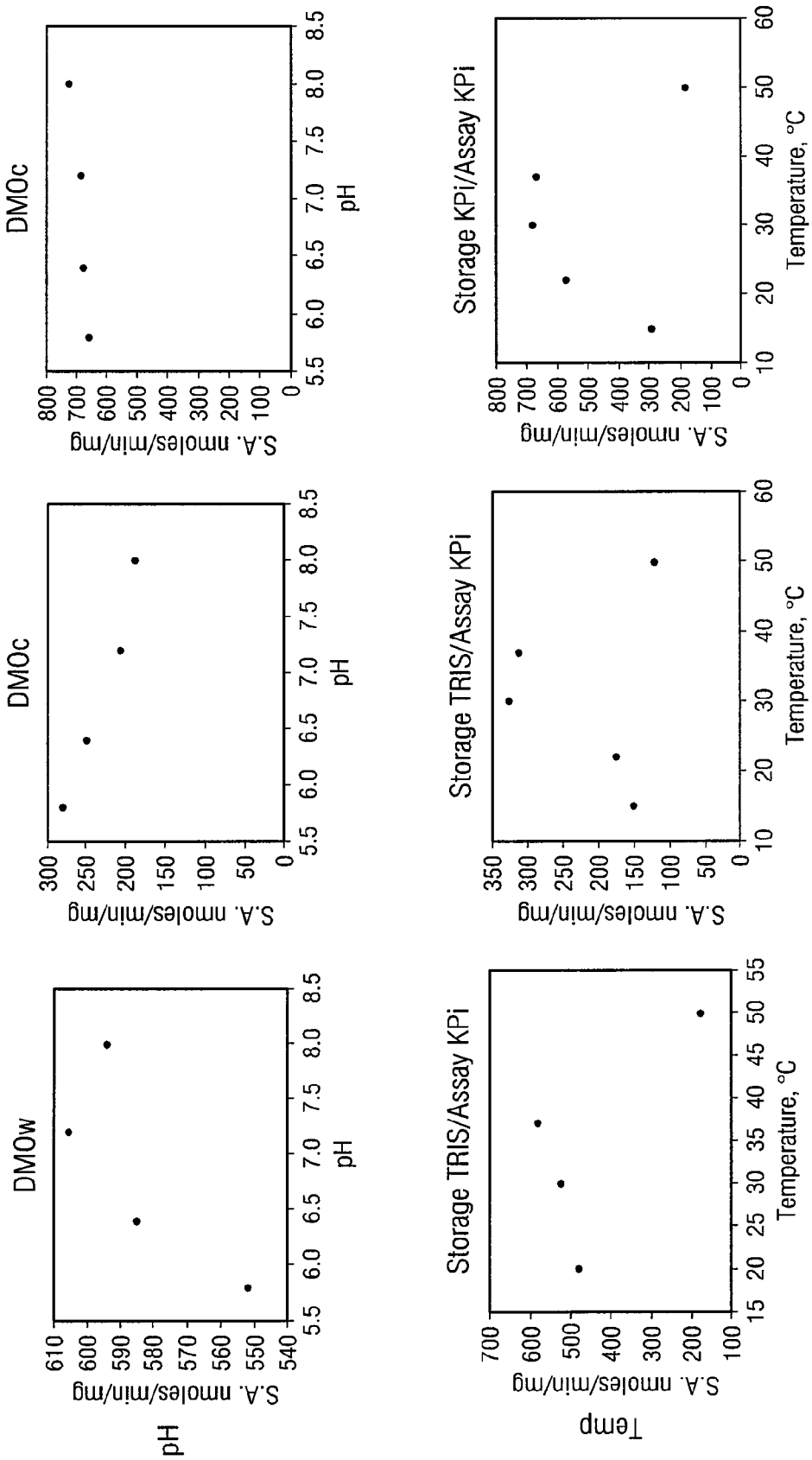
FIG. 9. Summary of temperature and pH optimum conditions for DMOc and DMOw.
Figure 12:
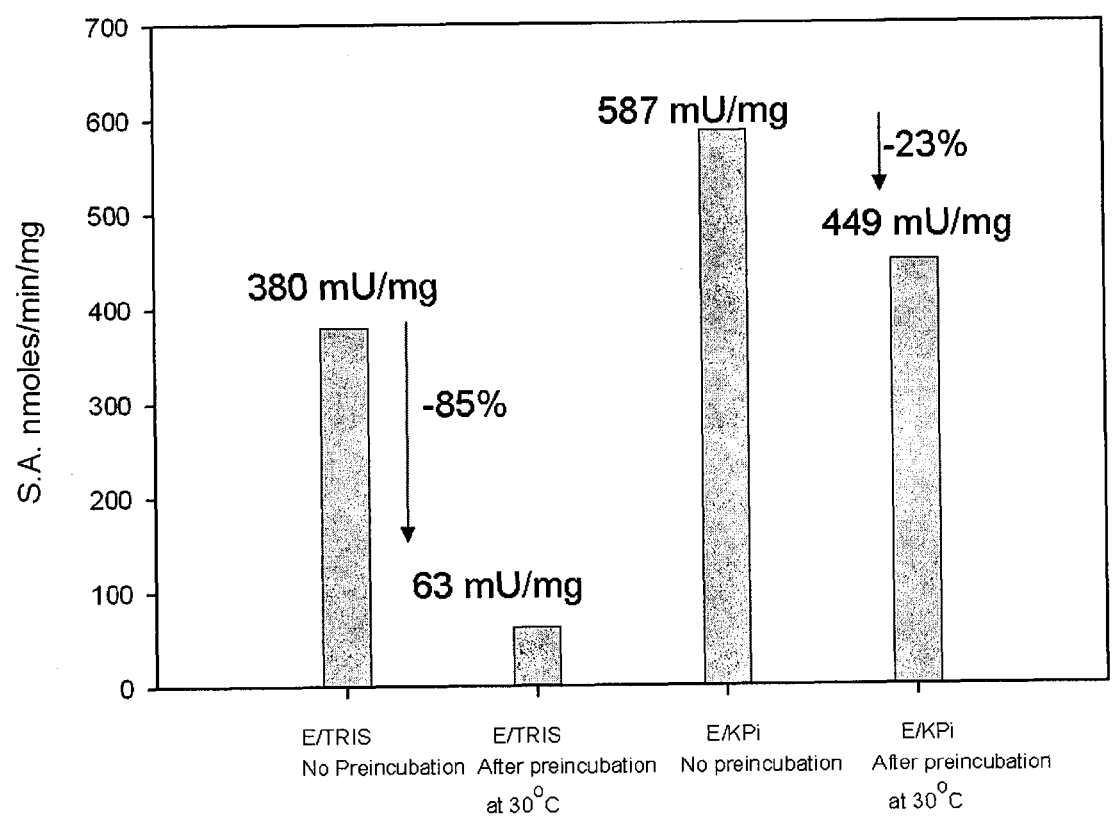
FIG. 12. Effects of preincubation of DMOc for 45 minutes at 30° C. in 50 mM TRIS pH7.5 and 100 mM KPi pH 7.0.
Figure 13:
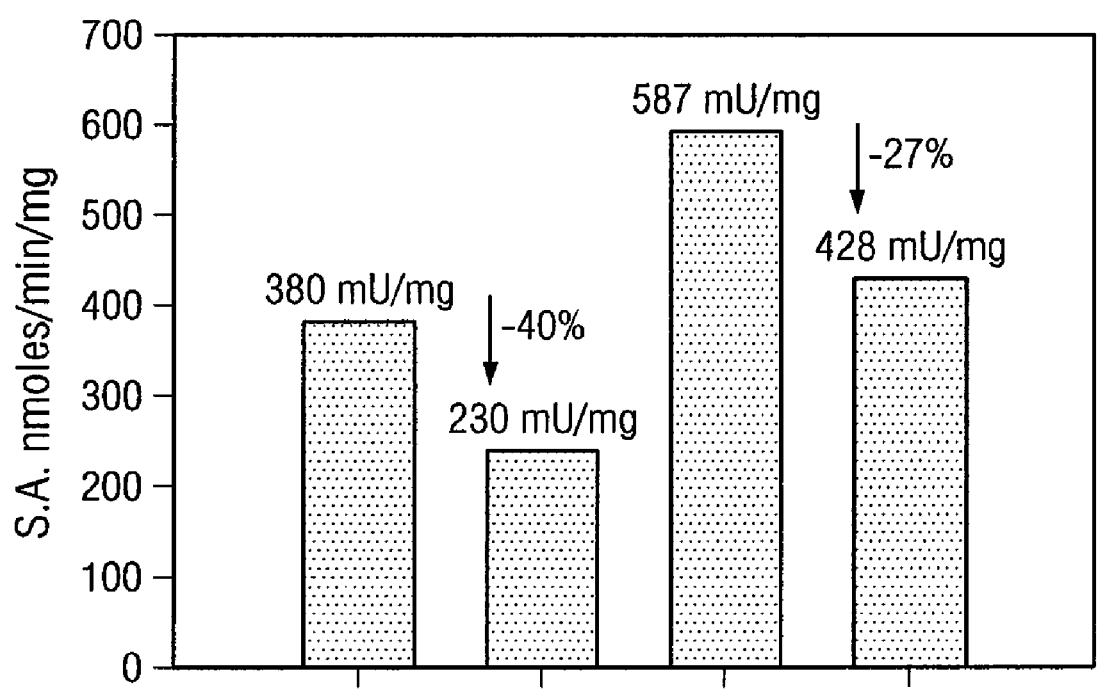
FIG. 13. DMOc assays with the enzyme sitting one week and stored at 4° C. in TRIS buffer (two assays to the left; assays before and after storage, respectively) and KPi buffer (two assays to the right; assays before and after storage, respectively).

As can be seen, in terms of catalytic efficiencies the DMOw and DMOc enzymes have different properties: DMOc is a five times better enzyme than DMOw by this analysis. The pH profile for DMOc is different that than of DMOw. First, DMOc appears to be sensitive to the buffering system used (TRIS vs. KPi) by comparison to DMOw (FIG. 9, 12, and 13). Second, DMOc exhibits a steady activity over a broad range of pHs when assayed in KPi buffer by comparison with TRIS when activity of DMOc decreases with increases in pH units. The temperature profiles for DMOc incubated in KPi or TRIS buffers are similar.

Looking at temperature profiles between these two forms of the enzyme, DMOw functioned better at 37° C. while DMOc functioned better at somewhat lower temperatures (FIG. 9). FIG. 9 indicates a lower temperature optima for DMOc, which may be useful in transgenic plants early in the growing season.

TABLE 1

The steady state kinetic parameters for DMOw and DMOc.

| Enzyme | Km (M) | Vmax (U/mg) | kcat (s$^{-1}$) | Kcat/Km (M$^{-1}$s$^{-1}$) |
|---|---|---|---|---|
| DMOw | 49 ± 7 × 10$^{-6}$ | 633 ± 24 × 10$^{-3}$ | 36.63 | 7.47 × 10$^5$ |
| DMOc | 20 ± 5 × 10$^{-6}$ | 676 ± 37 × 10$^{-3}$ | 70.41 | 35.21 × 10$^5$ |

TABLE 2

Summary of Michaelis-Menten parameters for DMOw.

| Study no. | Rsqr | Vmax (nmoles/min/mg) | Km (µM) |
|---|---|---|---|
| 1. | 0.983 | 633 ± 24 | 49 ± 7 |
| 2. | 0.988 | 583 ± 18 | 46 ± 5 |
| 3. | 0.987 | 590 ± 19 | 46 ± 5.5 |

TABLE 3

Summary of Michaelis-Menten parameters for DMOc.

| Study no. | Rsqr | Vmax (nmoles/min/mg) | Km (µM) |
|---|---|---|---|
| 1. | 0.933 | 713 ± 43 | 21 ± 6 |
| 2. | 0.948 | 676 ± 37 | 20 ± 5 |

Example 4

Bioinformatic Analysis of Conserved Regions of DMO

A bioinformatic analysis was carried out to compare the polypeptide sequence of DMO to other iron-sulfur oxygenases and to identify conserved regions. Initially, 78 sequences were selected for analysis based on an e-value cutoff of 1e-08 and 70% DMO sequence coverage on the sequence alignment. Further analysis of these 78 sequences revealed the presence of two domains that had been identified in other studies, including Rieske and non-haem Fe domains (Herman et al., 2005). Of these 78 sequences, 68 contained both domains, while 10 had only one of the domains. The 68 molecules with the two domains were used for further motif analysis.

Alignment of the 68 molecules with both domains in different identity levels revealed a new WXWX motif. While some sequences did not contain the motif, phylogenetic analysis indicated that the molecules without the motif fell into certain clades in phylogenetic tree that do not belong to the same group as the molecules with the motif. Those sequences without the motif were therefore removed from the original dataset, leaving 52 remaining sequences that were re-aligned for further analysis.

The re-aligned 52 sequences showed conservation around two W residues containing the following format: $WX_1WX_2G$ (W is Trp, G is Gly residue, $X_1$ is a non-polar residue, and $X_2$ is any amino acid). The second W in this case corresponds to position 112 of SEQ ID NO:1. The WXG of $WX_1WX_2G$ motif has been reported recently and proteins with the WXG motif are related to cellular secretion systems (Desvaux et al., 2005).

Tryptophan (W) and cysteine (C) are residues with remarkably different sizes. W is a large residue, while C is a relatively small one. Since both W and C are polar amino acids, they share some common characters, such as proton donation. As W residue is encoded by TGG and Cys by TGC and TGT, certain conversions in the third code (G->C or G->T) can yield a mis-sense mutation from the W to C or from C to W. Such conversions have been identified in nature and biofunctions and activities were changed by those mutations (see, e.g. BRCA1 gene in hereditary breast and ovarian cancer (Xiaoman and Jinghe, 1999); coagulation factor XII deficiency (Wada et al., 2003), and Lipoprotein lipase mutation in Type I hyperlipoproteinemia (Hoffmann et al., 2000)).

The foregoing results therefore indicated that, while DMO is unique and has low identity to known enzymes, W112 is conserved in other related iron-sulfur oxygenases. In addition, the 112 position is bounded by two conserved functional domains (FIG. 18). Further, W to C conversions typically affect bioactivity. The finding that DMOc yielded a functional enzyme with superior kinetic parameters than the wild-type DMOw enzyme and provided high-level tolerance to dicamba when expressed in transgenic plants was thus particularly surprising.

Example 5

Chloroplast Encoded DMO Yielded High-level Dicamba-resistance

Figure 14:
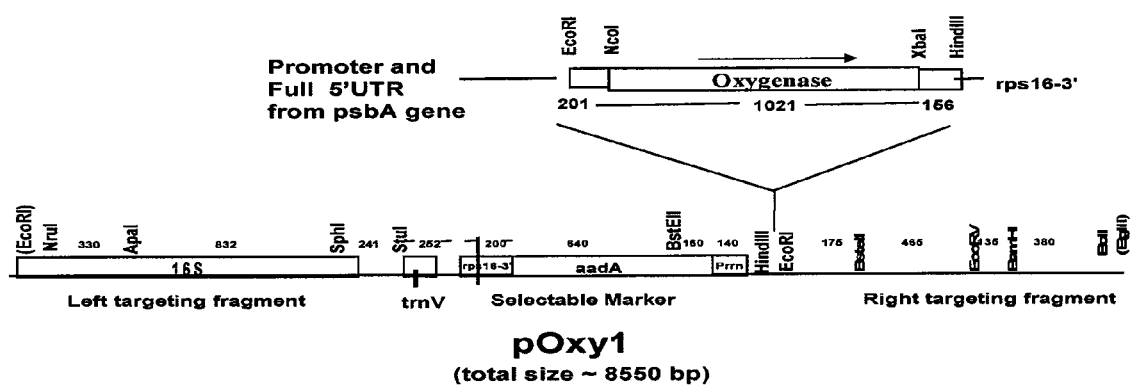
FIG. 14. Construct of dicamba monooxygenase gene genetically engineered for homologous recombination and expression in tobacco chloroplasts.
Figure 15:
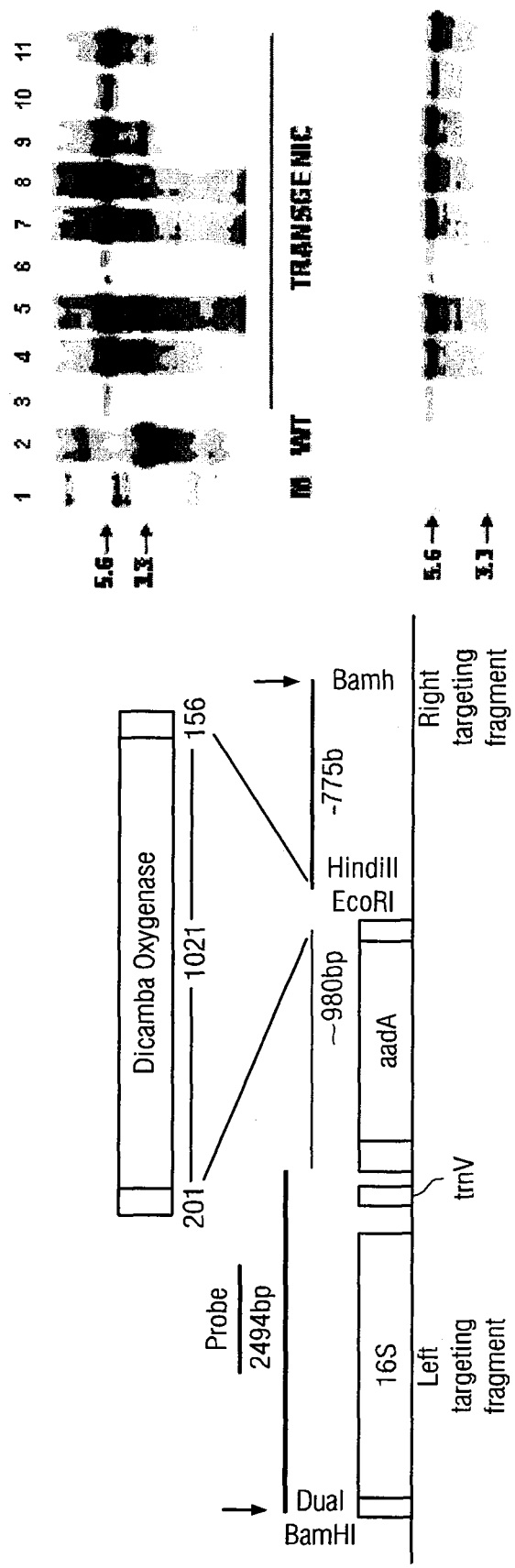
FIG. 15. Demonstration of homoplastidic status of chloroplast genomes of transgenic tobacco lines transformed with a DMO gene designed for homologous recombination and expression in tobacco chloroplasts. Left panel shows a construct for integration of DMO into chloroplast by homologous recombination (as shown in FIG. 14). Bar above the left targeting sequence denotes DNA fragment amplified for preparation of digoxigenin-labeled hybridization probe. Right panels show DNA blots: Lane 1 contains size-markers. Lane 2 contains DNA from nontransgenic tobacco plants. Lanes 3-11 contain DNA isolated from transgenic plants soon after first round of selection and regeneration in the presence of spectinomycin (upper panel) and after several rounds of selection and regeneration when apparent homoplastidity of the chloroplast genome was obtained (lower panel). DNA for DNA blot analyses was isolated from transgenic and nontransgenic plants and subjected to restriction enzyme digestion with BamH I prior to electrophoretic separation and probing of blotted DNA with a labeled DNA fragment complementary to the "left targeting sequence" of the chloroplast genome transformation vector (i.e., the digoxigenin-labeled hybridization probe). The 5.6 kb DNA band corresponds to chloroplast DNA fragment containing DMO gene and 3.3 kb band corresponds to homologous native chloroplast band lacking an inserted DMO gene construct.

To determine if DMO could function exclusively inside chloroplasts and to explore the possibility of limiting "gene spread" through pollen drift, constructs were created based on the pFMDVI vector (e.g., Svab et al., 1990) to allow integration of the DMOc gene into the chloroplast genome of tobacco by homologous recombination and isolation of transformants using selection for antibiotic resistance (FIG. 14). In this construct, the DMOc gene coding region is driven by the psbA chloroplast gene promoter containing the complete psbA 5' UTR sequence. Initial DNA blot analyses of antibiotic-resistant transgenic plants (FIG. 15A) demonstrated the presence in chloroplast genomes of both the DMOc transgene (5.6 kb band) and the native gene region (3.3 kb band) replaced by homologous integration of the DMOc gene (i.e., the chloroplasts were heteroplastidic for the native gene and the DMOc transgene). Repeated regeneration and selection of transgenic plants on antibiotic-containing medium resulted in apparently homoplastidic chloroplasts bearing the DMOc gene fragment but not the replaced native gene region (FIG. 15B).

Figure 16:
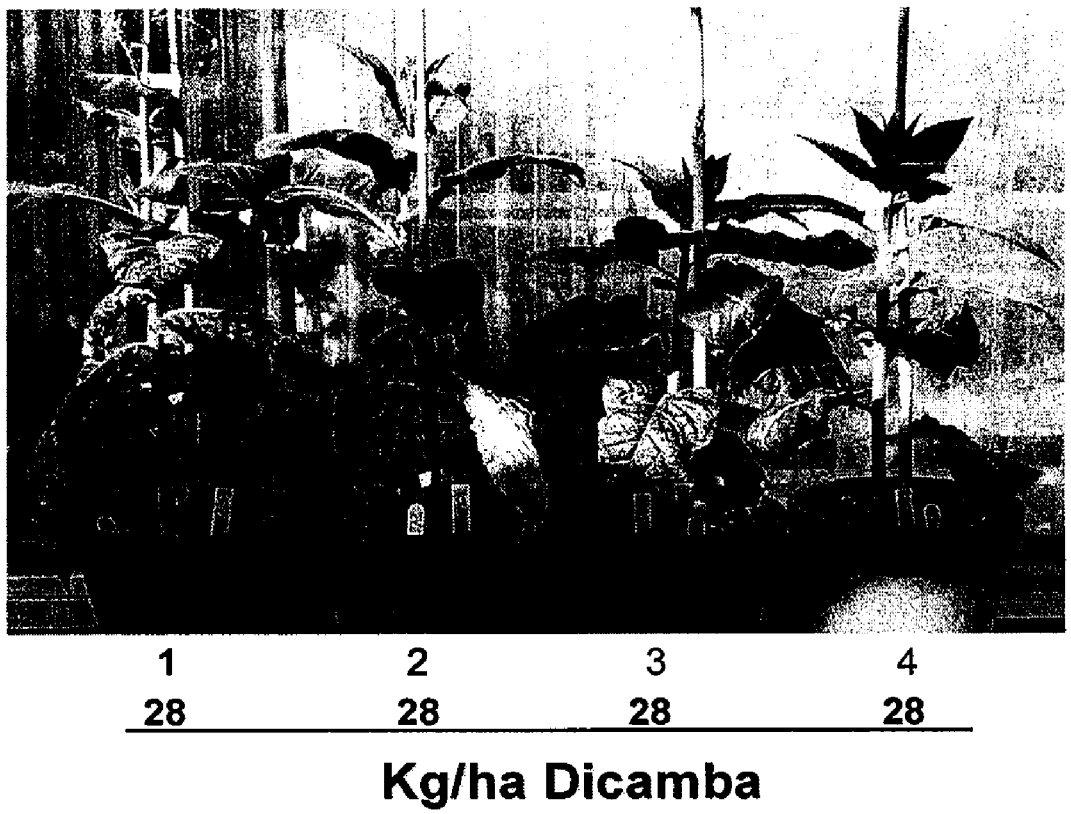
FIG. 16. $T_1$ generation homoplastidic transgenic tobacco plants containing a chloroplast-encoded dicamba monooxygenase gene treated with dicamba at a level of 28 kg/ha (Plants 1-2 and plants 3-4 were derived from two independently transformed $R_0$ plants.)
Figure 17:
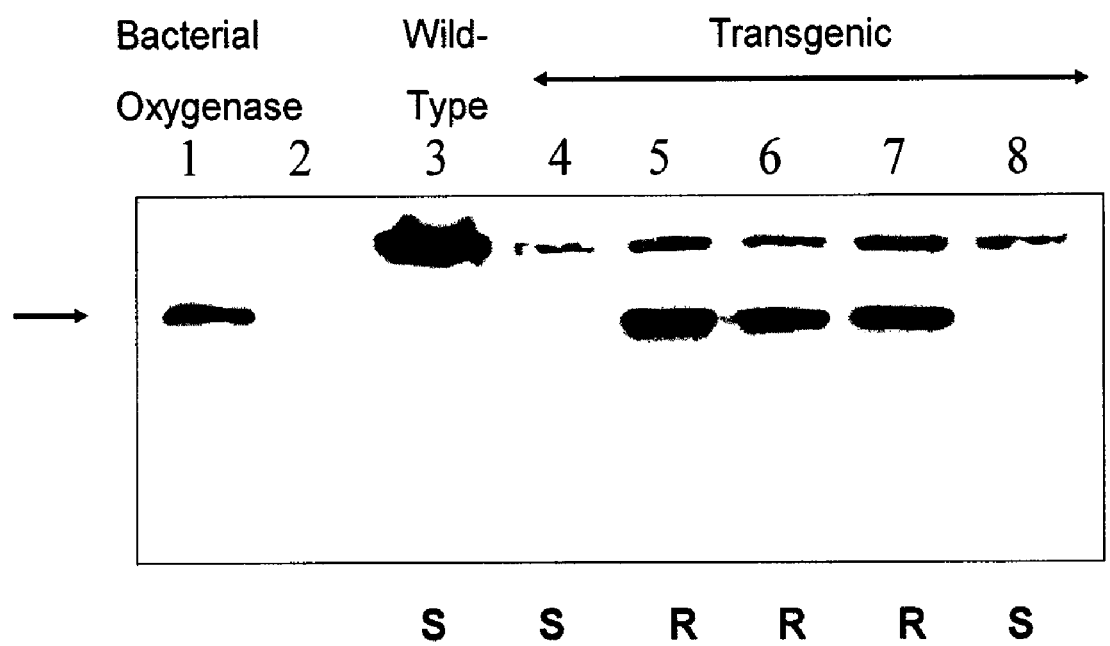
FIG. 17. Expression of DMO and sensitivity and resistance to dicamba treatment in nontransgenic and transgenic tobacco plants containing DMO gene in the chloroplast genome. Protein blot probed with DMO antibodies: Lane 1 contains purified DMO. Lane 2 is blank and lane 3 contains protein extracts from nontransgenic tobacco plants. Lanes 4 and 8 contain proteins isolated from "false-positive" tobacco plants displaying antibiotic resistance during selection on spectinomycin, but lacking intact DMO gene. Lanes 5-7 contain extracts of transgenic plants expressing DMO encoded by DMO gene integrated into the chloroplast genome. S=plants sensitive to dicamba at 0.56 kg/ha; R=plants resistant to dicamba at 5.6 kg/ha. Nearly equal amounts of extracts were loaded into lanes 4-8 as judged by amount of Rubisco large subunit protein detected with anti-Rubisco antibodies while significantly more protein from nontransgenic plants was loaded into lane 3. Arrow indicates the position of DMO protein.

$T_1$, $T_2$ and $T_3$ generations of progeny from two independently-derived chloroplast transformants were tested for tolerance to treatment with dicamba at various doses. All exhibited high levels of tolerance. Indeed, chloroplast genome transformants displayed no apparent damage (other than "solvent-only damage" to lower leaves) when sprayed with dicamba at a rate of 28 kg/ha (25 lb/ac) (FIG. 16) and only transitory damage was observed when plants were treated with extremely high dicamba applications of 112 and 224 kg/ha. At these extremely high levels, initial damage was caused primarily by surfactants and other components of the solvent in which dicamba was delivered; tissues growing from the damaged apex displayed nearly normal to normal phenotypes, showed no decrease in growth rates after initial stunting and retained the ability to produce usual numbers and quality of seeds.

The results were consistent with the possibility that reduced ferredoxin in tobacco chloroplasts could be the donor to DMO of electrons needed for oxidation of dicamba to DCSA. As a direct test of this possibility, the ability of purified spinach ferredoxin to support the conversion of dicamba to DCSA was examined in the presence and absence of DMO purified from *P. maltophilia*, strain DI-6, or overproduced and purified from *E. coli* (Table 4). The results demonstrated that reduced ferredoxin from spinach or *Clostridium* was fully capable of donating electrons to DMO in vitro as measured either by dicamba degradation or DCSA appearance.

Tables 4A-B. Purified dicamba monooxygenase can utilize reduced chloroplast ferredoxin or reduced Clostridium ferredoxin as a source of electrons to catalyze the conversion in vitro of dicamba to 3,6-dichlorosalicylic acid.

TABLE 4A

Degradation of Dicamba

| Type of Reaction | Degradation of Dicamba (%) |
|---|---|
| $(Ferr + Red)_{DI-6}$ + NADH | 0 |
| $(Oxy + Ferr + Red)_{DI-6}$ + NADH | 86 |
| $(Oxy)_{DI-6}$ + $(Ferr)_{spinach}$ + $(Ferr:Oxidored)_{spinach}$ + NADPH | 83 |
| $(Oxy)_{DI-6}$ + $(Ferr:Oxidored)_{spinach}$ + NADPH | ND |
| $(Oxy)_{DI-6}$ + $(Ferr)_{spinach}$ + $(Ferr:Oxidored)_{spinach}$ + No NADPH | ND |
| $(Oxy)_{DI-6}$ + $(Ferr)_{clostridium}$ + $(Ferr:Oxidored)_{spinach}$ + NADPH | 82 |
| $(Ferr)_{clostridium}$ + $(Ferr:Oxidored)_{spinach}$ + NADPH | ND |

TABLE 4B

Formation of DCSA

| Type of Reaction | Formation of DCSA (%) |
|---|---|
| (Ferr + Red)$_{DI-6}$ + NADH | ND |
| (Oxy + Ferr + Red)$_{DI-6}$ + NADH | 100 |
| (Oxy)$_{DI-6}$ + (Ferr)$_{spinach}$ + (Ferr:Oxidored)$_{spinach}$ + NADPH | 95 |
| (Oxy)$_{DI-6}$ + (Ferr:Oxidored)$_{spinach}$ + NADPH | 2.5 |
| (Oxy)$_{DI-6}$ + (Ferr)$_{spinach}$ + (Ferr:Oxidored)$_{spinach}$ + No NADPH | 1.2 |
| (Oxy)$_{DI-6}$ + (Ferr)$_{clostridium}$ + (Ferr:Oxidored)$_{spinach}$ + NADPH | 90 |
| (Ferr)$_{clostridium}$ + (Ferr:Oxidored)$_{spinach}$ + NADPH | 1.5 |

ND, Not Determined

While the results in FIG. 2 showed that DMO levels produced were variable and sometimes DMOc levels did not closely correlate with dicamba tolerance levels, the results demonstrated the ability to consistently obtain high-level tolerance to dicamba. Production of DMOc from both a nuclear located DMOc gene and from a chloroplastic located DMOc gene in transformants was shown. In nuclear transformants none constituted an exceptionally high level of total DMOc relative to total protein and the amount of DMOc in chloroplast transformants was not greatly different and sometimes lower than nuclear transformants. Estimates of the relative enzymatic activity in cell free extracts of leaf tissue samples indicated that a higher percentage of DMOc produced in the chloroplasts is active than DMOc synthesized in the cytoplasm and assumedly transferred to the chloroplasts.

In all of the plants analyzed dicamba tolerance was achieved without cotransformation with either ferredoxin or reductase genes. The results demonstrated that the plants contained one or more molecules that could transfer requisite electrons to DMO to allow conversion of dicamba to 3,6-dichlorosalicylic acid (DCSA). The initial targeting of DMO to the chloroplasts using a transit peptide sequence was aimed at potentially utilizing reduced ferredoxin abundantly available in the chloroplasts. In this regard, it is of interest to note that transformation of tobacco plants with a DMOc gene construct lacking a chloroplast peptide coding sequence unexpectedly resulted in plants that were tolerant to post-emergent treatment with dicamba. Results from limited trials with a small number of $T_1$ generation plants, nonetheless, indicated the level of tolerance obtained with these transgenic plants was slightly lower on average than that obtained with tobacco plants producing DMOc containing a transit peptide. These observations raise interesting questions in regard to the molecules in transgenic plants that can productively donate electrons to DMO. The fact that homoplastidic chloroplasts producing DMO internally from a DMOc gene integrated into the chloroplast genome show resistance to extremely high levels of dicamba (FIG. 16) and the fact that purified DMO can function in vitro with reduced spinach chloroplast ferredoxin (Table 4) both suggest that chloroplast ferredoxin can productively interact with DMO to allow electron transfer. However, the source of electrons for DMO produced from nuclear genes lacking a chloroplast transit peptide coding sequence remains unknown. Presuming that ferredoxins do not reside outside of the plant chloroplasts, one must consider the possibility that an unknown cytoplasmic protein can provide DMO with a steady supply of electrons. Alternatively, DMO, itself, might contain a gratuitous chloroplast transit peptide that allows sufficient DMO to enter the chloroplasts to provide protection from dicamba moving into the cell after dicamba treatment.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. Nos. 4,554,101; 4,940,838; 5,015,580; 5,017,692; 5,229,114; 5,304,730; 5,322,938; 5,352,605; 5,359,142; 5,362,865; 5,378,619; 5,384,253; 5,445,962; 5,463,175; 5,464,763; 5,508,184; 5,512,466; 5,516,671; 5,530,196; 5,538,880; 5,543,576; 5,550,318; 5,552,299; 5,567,600; 5,567,862; 5,591,616; 5,633,435; 5,635,055; 5,641,876; 5,659,122; 5,689,041; 5,689,052; 5,716,837; 5,728,925; 5,750,876; 5,763,241; 5,763,245; 5,773,696; 5,804,425; 5,824,877; 5,837,848; 5,850,019; 5,850,023; 5,866,775; 5,869,720; 5,880,275; 5,942,658; 5,942,664; 5,958,745; 5,959,091; 5,981,834; 5,981,840; 5,985,605; 5,998,700; 6,011,199; 6,013,864; 6,015,940; 6,023,013; 6,051,753; 6,063,597; 6,063,756; 6,072,103; 6,080,560; 6,093,695; 6,107,549; 6,110,464; 6,121,436; 6,140,075; 6,140,078; 6,153,814; 6,156,573; 6,160,208; 6,166,292; 6,171,640; 6,175,060; 6,177,611; 6,177,615; 6,215,048; 6,221,649; 6,222,098; 6,225,114; 6,228,623; 6,228,992; 6,232,526; 6,235,971; 6,242,241; 6,248,536; 6,248,876; 6,252,138; 6,271,443; 6,281,016; 6,284,949; 6,294,714; 6,313,378; 6,316,407; 6,326,351; 6,372,211; 6,380,462; 6,380,466; 6,384,301; 6,399,330; 6,399,861; 6,403,865; 6,423,828; 6,426,446; 6,426,447; 6,429,357; 6,429,362; 6,433,252; 6,437,217; 6,441,277; 6,444,876; 6,448,476; 6,459,018; 6,468,523; 6,476,295; 6,483,008; 6,489,461; 6,495,739; 6,501,009; 6,506,962; 6,518,488; 6,521,442; 6,531,648; 6,537,750; 6,537,756; 6,538,109; 6,538,178; 6,538,179; 6,538,181; 6,541,259; 6,555,655; 6,573,361; 6,576,818; 6,589,767; 6,593,293; 6,596,538; 6,608,241; 6,617,496; 6,620,988; 6,635,806; 6,639,054; 6,642,030; 6,645,497; 6,653,280; 6,653,530; 6,657,046; 6,660,849; 6,663,906; 6,686,452; 6,706,950; 6,713,063; 6,716,474; 6,723,837; 6,723,897; 6,770,465; 6,774,283; 6,803,501; 6,809,078; 6,812,379; 6,822,141; 6,828,475; 7,022,896; U.S. Patent Pub. 2003/0028917; U.S. Patent Pub. 2003/0135879; U.S. Patent Pub. 2003/01403641; U.S. patent Ser. No. 09/757,089; U.S. Pat. Nos. RE37,543; RE38,446

Ausubel et al., In: Current Protocols in Molecular Biology, John, Wiley & Sons, Inc, New York, 1995.
Becker et al. Plant Mol. Biol. 20:1195-1197, 1992
Becker et al., Plant Mol. Biol., 20:49, 1992.
Bevan et al., NAR, 11:369, 1983.
Brothers et al, Nature, 433:630, 2005.
Carrington and Freed, J. of Virology 64:1590-1597, 1990
Carrington and Freed, J. Virology, 64:1590, 1990.

Chalfie et al., *Science*, 263:802, 1994.
Chandler et al., *Plant Cell*, 1:1175-1183, 1989.
Chang et al., *J. Biol. Chem.*, 31;278(44):42821-42828, 2003.
Chu et al., *Scientia Sinica*, 18:659, 1975.
Clough and Bent, *Plant J.*, 16:735, 1998.
Cork and Khalil, *Adv. Appl. Microbiol.*, 40: 289, 1995.
Cork and Krueger, *Adv. Appl. Microbiol.*, 38:1, 1991.
Coruzzi et al., *EMBO J.*, 3: 1671, 1984.
Coruzzi et al., *J. Biol. Chem.* 258:1399-1402, 1983
Creissen et al., Plant J., 2:129, 1991.
Crop Protection Reference, Chemical & Pharmaceutical Press, Inc., NY, 11th Ed., 1803-1821, 1995
De Block et al., *EMBO J.*, 3:1681, 1984.
della-Cioppa et al., *Proc. Natl. Acad. Sci. USA*, 83:6873-6877, 1986.
Depicker et al, *J. Mol. Appl. Genet.*, 1:561, 1982.
Desvaux et al., *Biochimica et Biophysica Acta*, 1745:223-253, 2005.
Ditta et al., *Proc. Natl. Acad. Sci. USA*, 77(12):7347-7351, 1980.
Ebert et al., *Proc. Natl. Acad. Sci. USA*, 84:5745-5749, 1987.
EP Appln. 553494
EP Appln. 646643
Fraley et al., *Proc. Natl. Acad. Sci. USA*, 80:4803, 1983.
Hajdukiewicz et al., *Plant Mol. Biol.* 25:989-994, 1994
Haseloff et al., *TIG*, 11:328-329, 1995.
Herman et al., *J. Biol. Chem.*, 280:24759-24767, 2005.
Hoffmann et al. *J. Clin. Endocrinol. Metab.*, 85(12):4795-498, 2000.
Horsch et al., *Science*, 227:1229, 1985.
Ingelbrecht et al., *Plant Cell*, 1:671, 1989.
Jefferson, *Plant Mol. Biol. Rep.*, 5:387, 1987.
Jiang et al., *J. Bacteriol.* 178:3133-3139, 1996.
Kado, *Crit. Rev. Plant. Sci.*, 10:1, 1991.
Klee et al., *Mol. Gen. Genet.*, 210:437-442, 1987.
Koncz and Schell, *Mol. Gen. Genet.*, 204:383 396, 1986.
Koncz et al., *Proc. Natl. Acad. Sci., USA*, 84:131, 1987.
Krueger et al., *J. Agric. Food Chem.*, 37:534, 1989.
Kyte and Doolittle, *J. Mol. Biol.*, 157(1):105-132, 1982.
Lawton et al., *Plant Mol. Biol.*, 9:315-324, 1987.
Lloyd and McCown, *Proc. Int. Plant Prop. Soc.*, 30:421, 1981.
Maniatis, et al., Molecular Cloning, A Laboratory Manual, Cold Spring Harbor Press, Cold Spring Harbor, N.Y., 1982.
Mason, J R, and Cammack, R., *Annu. Rev. Microbiol.* 46:277-305, 1992.
Miki et al., In: *Methods in Plant Molecular Biology and Biotechnology*, Glick and Thompson (Eds.), CRC Press, 67-88, 1993.
Mitsuhara et al., *Plant Cell Physiol.* 37:49-59, 1996
Moloney et al., *Plant Cell Reports*, 8:238, 1989.
Murashige and Skoog, *Physiol. Plant*, 15:473-497, 1962.
Odell et al., *Nature*, 313:810-812, 1985.
PCT Appln. WO 04009761
PCT Appln. WO 95/24492
PCT Appln. WO 97/11086
PCT Appln. WO 97/31115
PCT Appln. WO 97/41228
Rojiyaa et al., (JP 1987201527-A), 1987.
Sambrook et al., *In: Molecular cloning: a laboratory manual*, 2nd Ed., Cold Spring Harbor Laboratory Press, Cold Spring Harbor, N.Y., 1989.
Southern, *Mol. Biol.*, 98:503, 1975.
Svab et al., *Plant Mol. Biol.*, 14:197, 1990.
Svab et al., *Proc. Natl. Acad. Sci. USA*, 87(21):8526-8530, 1990.
Teeri et al., *EMBO J.*, 8:343, 1989.
Turner and Foster, *Molec. Biotechn.*, 3:225, 1995.
Wada et al., *Thromb. Haemost.*, 90(1):59-63, 2003.
Walker et al., *Proc. Natl. Acad. Sci. USA*, 84:6624-6628, 1987.
Xiaoman and Jinghe, *Chin. Med. Sci. J.*, 14(4):195-199, 1999.
Yang et al., *Proc. Natl. Acad. Sci. USA*, 87:4144-4148, 1990.
Zhang et al, *Plant Cell, Tissue and Organ Culture*, 56: 37-46, 1999.

---

What is claimed is:

1. A nucleic acid molecule selected from the group consisting of:
   a) a nucleic acid molecule encoding the polypeptide of SEQ ID NO:1;
   b) a nucleic acid molecule comprising the sequence of SEQ ID NO:2; and
   c) a nucleic acid molecule encoding a polypeptide with at least 90% sequence identity to the polypeptide of SEQ ID NO:1, wherein the polypeptide has dicamba monooxygenase activity and comprises cysteine at a position corresponding to amino acid 112 of SEQ ID NO:1.

2. The nucleic acid molecule of claim 1, wherein the nucleic acid molecule encodes the dicamba monooxygenase encoded by plasmid pKLP36-TEV-TP-DMOc (ATCC Accession No. PTA-7357).

3. A DNA construct comprising the nucleic acid molecule of claim 1 operably linked to a promoter.

4. The construct of claim 3, wherein the promoter is functional in a plant cell.

5. The construct of claim 3, wherein the nucleic acid molecule is operably linked to a chloroplast transit peptide.

6. A method of producing a dicamba tolerant plant comprising introducing into the plant the construct of claim 3.

7. The method of claim 6, comprising introducing said construct into said plant by stably transforming a starting plant cell and regenerating the cell into said dicamba tolerant plant.

8. The method of claim 6, wherein the dicamba tolerant plant is produced by crossing a parent plant with itself or a second plant, wherein the parent plant and/or the second plant comprises the transformation construct and the dicamba tolerant plant inherits the transformation construct from said parent plant and/or the second plant.

9. A plant cell transformed with the nucleic acid molecule of claim 1.

10. The cell of claim 9, wherein the plant cell is a dicotyledonous plant cell.

11. The cell of claim 10, wherein the dicotyledonous plant cell is a soybean, cotton, maize or rapeseed plant cell.

12. The cell of claim 9, wherein the plant cell is a monocotyledonous plant cell.

13. A plant tissue culture comprising the cell of claim 9.

14. A transgenic plant transformed with the nucleic acid molecule of claim 1.

15. The transgenic plant of claim 14, wherein the plant is a dicotyledonous plant.

16. The transgenic plant of claim 14, wherein the plant is a monocotyledonous plant.

17. The transgenic plant of claim 14, wherein the plant is a soybean, cotton, maize or rapeseed plant.

18. A method of controlling weed growth in a crop growing environment comprising a plant of claim 14 or a seed thereof, the method comprising applying to the crop growing environment an amount of dicamba herbicide effective to control weed growth.

19. The method of claim 18, wherein the dicamba herbicide is applied over the top to the crop growing environment.

20. The method of claim 18, wherein the amount of dicamba herbicide does not damage said plant or seed thereof and damages a plant of the same genotype as the plant lacking the nucleic acid.

21. A polypeptide sequence comprising an amino acid sequence with at least 90% identity to SEQ ID NO:1, wherein the polypeptide has dicamba monooxygenase activity and comprises cysteine at a position corresponding to amino acid 112 of SEQ ID NO:1.

22. A method of producing food, feed or an industrial product comprising:
   a) obtaining the plant of claim 14 or a part thereof; and
   b) preparing the food, feed or industrial product from the plant or part thereof.

23. The method of claim 22, wherein the food or feed is oil, meal, grain, starch, flour, or protein.

24. The method of claim 22, wherein the industrial product is biofuel, fiber, industrial chemicals, a pharmaceutical or nutraceutical.

* * * * *

UNITED STATES PATENT AND TRADEMARK OFFICE
CERTIFICATE OF CORRECTION

PATENT NO.        : 7,884,262 B2                                    Page 1 of 1
APPLICATION NO.   : 11/758657
DATED             : February 8, 2011
INVENTOR(S)       : Clemente et al.

It is certified that error appears in the above-identified patent and that said Letters Patent is hereby corrected as shown below:

On the Title page, item [73] for Assignee, add --; The Board of Regents of the University of Nebraska- -.

Signed and Sealed this
Twenty-seventh Day of October, 2015

Michelle K. Lee
*Director of the United States Patent and Trademark Office*

SEQUENCE LISTING

```
<160> NUMBER OF SEQ ID NOS: 24

<210> SEQ ID NO 1
<211> LENGTH: 340
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80
```

```
Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340

<210> SEQ ID NO 2
<211> LENGTH: 1023
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
atggccacct tcgtccgcaa tgcctggtat gtggcggcgc tgcccgagga actgtccgaa      60
aagccgctcg gccggacgat tctcgacaca ccgctcgcgc tctaccgcca gcccgacggt     120
gtggtcgcgg cgctgctcga catctgtccg caccgcttcg cgccgctgag cgacggcatc     180
ctcgtcaacg ccatctcca atgccccta cacgggctgg aattcgatgg cggcgggcag      240
tgcgtccata accogcacgg caatggcgcc cgcccggctt cgctcaacgt ccgctccttc     300
ccggtggtgg agcgcgacgc gctgatctgg atctgtccgg gcgatccggc gctgccgat      360 cctggggcga tccccgactt cggctgccgc gtcgatcccg cctatcggac cgtcggcggc     420
tatgggcatg tcgactgcaa ctacaagctg ctggtcgaca acctgatgga cctcggccac     480
gcccaatatg tccatcgcgc caacgcccag accgacgcct tcgaccggct ggagcgcgag     540
```

```
gtgatcgtcg gcgacggtga gatacaggcg ctgatgaaga ttcccggcgg cacgccgagc    600
gtgctgatgg ccaagttcct gcgcggcgcc aataccccg tcgacgcttg aacgacatc     660 cgctggaaca aggtgagcgc gatgctcaac ttcatcgcgg tggcgccgga aggcaccccg    720
aaggagcaga gcatccactc gcgcggtacc catatcctga cccccgagac ggaggcgagc    780
tgccattatt tcttcggctc ctcgcgcaat ttcggcatcg acgatccgga gatggacggc    840
gtgctgcgca gctggcaggc tcaggcgctg gtcaaggagg acaaggtcgt cgtcgaggcg    900
atcgagcgcc gccgcgccta tgtcgaggcg aatggcatcc gcccggcgat gctgtcgtgc    960
gacgaagccg cagtccgtgt cagccgcgag atcgagaagc ttgagcagct cgaagccgcc   1020
tga                                                                 1023

<210> SEQ ID NO 3
<211> LENGTH: 1023
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
atggccactt tcgttagaaa cgcttggtac gttgctgcac ttcctgagga gttgagcgag     60
aagcctctag gaagaactat cctcgatact ccactagctc tctatcgtca acctgacgga    120
gttgtcgctg ccctgcttga tatttgtccg catcgcttcg ctccgttgag tgacggtatt    180
ctagtcaacg gacatctcca gtgtccatat cacggtctgg aatttgacgg aggtggccag    240
tgtgtccaca acccgcacgg caacggagcc cgccctgctt ctctgaacgt gcgatcattc    300
cctgtcgtgg aaagagacgc attgatctgg atctgccctg gagatccagc actcgcagat    360
cccggtgcta tccctgactt tgggtgtcgt gttgatccag cttaccgtac tgtcggaggt    420
tacggtcacg tggactgcaa ctacaagctc cttgtggata acctcatgga tcttggacac    480
gctcagtacg tgcaccgcgc taacgcccaa acagacgcct tcgatagact tgagcgtgag    540
gtgatcgttg gcgacggcga gatccaggcg ctcatgaaga tccctggtgg cacaccctca    600
gttctcatgg ctaagttctt gcgtggtgct aacacaccag ttgacgcctg gaacgacatc    660
cggtggaata aggtgtcggc tatgctgaac ttcatcgcgg tcgcgccgga agggacgccg    720
aaggagcagt caatccactc ccgaggaacc catatcctta ctcctgagac cgaggcaagc    780
tgccattact tcttcggtag ttcccgcaac ttcggtatag acgatccaga gatggacggt    840
gttctcagga gctggcaagc tcaagccctg gtgaaggagg acaaagtggt cgttgaagct    900
atcgaaaggc ggagggctta cgtcgaagcg aacgggatca gacccgccat gttgtcctgc    960
gacgaggcag ccgtcagggt atccaggag attgagaagc tcgaacaact agaagcggcg   1020
tga                                                                 1023

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Ser Asp Ile Cys Pro His Arg Phe Ala Pro Leu His Leu Gly Lys Ile
  1               5                  10                  15
```

```
Val Asp Gly Cys Arg Ile Gln Cys Ala Tyr His Ala Leu Glu Phe Asp
            20                  25                  30

Gly Thr Gly Ala Cys Val Lys Asn Pro His Gly Lys Gln Lys Ile Pro
        35                  40                  45

Ala Ala Ala Lys Leu Gln Ala Tyr Pro Val Val Glu Lys His Ser Leu
    50                  55                  60

Ile Trp Val Trp Met Gly Glu Gln Ala Ala Asp Pro Ser Val Ile
65              70                  75                  80

Pro Asp Phe Ser Met Leu Asp Pro Asp Ser Gly Phe Gln Val Ser Arg
                85                  90                  95

Arg Asp Trp Leu His Met Asp Ala Ser Tyr Asp Leu Val Val Asp Asn
            100                 105                 110

Leu Met Asp Leu Ser His Thr Ala
        115                 120
```

<210> SEQ ID NO 5
<211> LENGTH: 58
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

```
Ala Asp Arg Cys Pro His Arg Phe Val Pro Leu Ser Arg Gly Gln Arg
1               5                   10                  15

Asp Gly Asp Met Met Arg Cys Gly Tyr His Gly Leu Ala Phe Ser Ser
            20                  25                  30

Ser Gly Gly Cys Val His Asn Pro Phe Thr Asp Glu Ala Leu Pro Leu
        35                  40                  45

Ala Arg Val Glu Val Leu Pro Val Val Glu
    50                  55
```

<210> SEQ ID NO 6
<211> LENGTH: 58
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

```
Gly Gly Arg Cys Pro His Arg Phe Ala Pro Leu Gly His Gly Ser Val
1               5                   10                  15

Val Asp Gly Ala Leu Met Cys Pro Tyr His Gly Leu Arg Phe Asp Gly
            20                  25                  30

Asp Gly Arg Cys Val His Asn Pro His Pro Gly Gly His Leu Pro Asp
        35                  40                  45

Ala Arg Gln Arg Val Tyr Pro Leu Val Glu
    50                  55
```

<210> SEQ ID NO 7
<211> LENGTH: 59
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

-continued

Leu Asp Ile Cys Pro His Arg Phe Ala Pro Leu Ser Asp Gly Ile Leu
1               5                   10                  15

Val Asn Gly His Leu Gln Cys Pro Tyr His Gly Leu Glu Phe Asp Gly
            20                  25                  30

Gly Gly Gln Cys Val His Asn Pro His Gly Asn Gly Ala Arg Pro Ala
        35                  40                  45

Ser Leu Asn Val Arg Ser Phe Pro Val Val Glu
    50                  55

<210> SEQ ID NO 8
<211> LENGTH: 57
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Glu Asp Phe Cys Pro His Arg Gly Ala Pro Leu Ser Leu Gly Phe Val
1               5                   10                  15

Arg Asp Gly Val Leu Val Cys Gly Tyr His Gly Leu Glu Met Gly Cys
            20                  25                  30

Asn Gly Lys Thr Ala Ala Met Pro Gly Gln Arg Val Gly Gly Phe Pro
        35                  40                  45

Ala Ile Arg Ser Phe Pro Val Val Glu
    50                  55

<210> SEQ ID NO 9
<211> LENGTH: 57
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Glu Asp Phe Cys Pro His Arg Gly Ala Pro Leu Ser Leu Gly Phe Val
1               5                   10                  15

Arg Asp Gly Val Leu Val Cys Gly Tyr His Gly Leu Glu Met Gly Cys
            20                  25                  30

Asn Gly Lys Pro Ala Gly Met Pro Gly Gln Arg Val Gly Gly Phe Pro
        35                  40                  45

Ser Ile Arg Ser Phe Pro Ala Val Glu
    50                  55

<210> SEQ ID NO 10
<211> LENGTH: 57
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Glu Asp Phe Cys Pro His Arg Gly Ala Pro Leu Ser Leu Gly Phe Val
1               5                   10                  15

Arg Asp Gly His Leu Val Cys Gly Tyr His Gly Leu Thr Met Lys Ala
            20                  25                  30

Asp Gly Lys Cys Ala Ser Met Pro Gly Gln Arg Val Gly Gly Phe Pro
        35                  40                  45

Cys Ile Arg Gln Phe Pro Val Val Glu

<210> SEQ ID NO 11
<211> LENGTH: 57
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 11

Glu Asp Phe Cys Pro His Arg Gly Ala Pro Leu Ser Leu Gly Phe Val
 1               5                  10                  15

Arg Asp Gly Gln Leu Val Cys Gly Tyr His Gly Leu Glu Met Gly Cys
            20                  25                  30

Asp Gly Lys Cys Ser Ser Met Pro Gly Gln Arg Val Arg Gly Phe Pro
        35                  40                  45

Ser Ile His Ala Tyr Pro Val Val Glu
    50                  55

<210> SEQ ID NO 12
<211> LENGTH: 58
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 12

Glu Asp Ala Cys Trp His Arg Leu Val Pro Leu Ser Lys Gly Arg Leu
 1               5                  10                  15

Glu Gly Asp Thr Val Val Cys Gly Tyr His Gly Leu Lys Phe Asn Pro
            20                  25                  30

Gln Gly Arg Cys Thr Tyr Met Pro Ser Gln Glu Thr Ile Asn Pro Ser
        35                  40                  45

Ala Cys Val Arg Ser Tyr Pro Val Val Glu
    50                  55

<210> SEQ ID NO 13
<211> LENGTH: 58
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 13

Glu Asp Ala Cys Trp His Arg Leu Val Pro Leu Ser Lys Gly Arg Leu
 1               5                  10                  15

Glu Gly Asp Thr Val Val Cys Gly Tyr His Gly Leu Lys Tyr Asn Ala
            20                  25                  30

Gln Gly Arg Cys Thr Phe Met Pro Ser Gln Glu Thr Ile Asn Pro Ser
        35                  40                  45

Ala Cys Val Arg Ala Tyr Pro Val Val Glu
    50                  55

<210> SEQ ID NO 14
<211> LENGTH: 60
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 14

Lys His Ser Leu Ile Trp Val Trp Met Gly Glu Gln Ala Ala Ala Asp
1               5                   10                  15

Pro Ser Val Ile Pro Asp Phe Ser Met Leu Asp Pro Asp Ser Gly Phe
            20                  25                  30

Gln Val Ser Arg Arg Asp Trp Leu His Met Asp Ala Ser Tyr Asp Leu
        35                  40                  45

Val Val Asp Asn Leu Met Asp Leu Ser His Thr Ala
    50                  55                  60

<210> SEQ ID NO 15
<211> LENGTH: 57
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 15

Lys His Thr Gly Leu Trp Phe Trp Pro Gly Asp Ala Asp Arg Ala Asp
1               5                   10                  15

Pro Ala Leu Ile Pro Asp Phe Gly Phe Leu Asp Val Glu Arg Pro Leu
            20                  25                  30

His Arg Gly His Leu Lys Met Asp Ala Gly Tyr Glu Leu Val Thr Asp
        35                  40                  45

Asn Leu Met Asp Leu Ser His Ala Glu
    50                  55

<210> SEQ ID NO 16
<211> LENGTH: 58
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 16

Arg His Ala Leu Leu Trp Ile Trp Met Gly Asp Ala Ala Lys Ala Asp
1               5                   10                  15

Pro Ala Ser Ile Pro Asp Phe Ser Trp Leu Ser Asp Pro Arg Trp Glu
            20                  25                  30

Ala Val Arg Gly Ala Thr Val Ala Glu Gly His Phe Glu Leu Tyr Ser
        35                  40                  45

Asp Asn Ile Leu Asp Leu Ser His Ala Asn
    50                  55

<210> SEQ ID NO 17
<211> LENGTH: 58
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 17

Arg Asp Ala Leu Ile Trp Ile Trp Pro Gly Asp Pro Ala Leu Ala Asp
1               5                   10                  15

Pro Gly Ala Ile Pro Asp Phe Gly Cys Arg Val Asp Pro Ala Tyr Arg
            20                  25                  30

Thr Val Gly Gly Tyr Gly His Val Asp Cys Asn Tyr Lys Leu Leu Val

```
              35                  40                  45

Asp Asn Leu Met Asp Leu Gly His Ala Gln
    50                  55

<210> SEQ ID NO 18
<211> LENGTH: 58
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 18

Arg Tyr Gly Phe Val Trp Val Trp Pro Gly Asp Ala Ser Arg Ala Asp
 1               5                  10                  15

Pro Ala Ala Leu Pro Ala Leu Thr Trp Ala Asp Asp Pro Val Trp Ala
            20                  25                  30

His Gly Gly Gly Leu Tyr His Ile Arg Cys Asp Tyr Arg Leu Met Ile
        35                  40                  45

Asp Asn Leu Met Asp Leu Thr His Glu Thr
    50                  55

<210> SEQ ID NO 19
<211> LENGTH: 58
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 19

Arg Tyr Gly Phe Val Trp Val Trp Pro Gly Asp Ala Ser Glu Ala Asp
 1               5                  10                  15

Pro Ala Lys Leu Pro Ala Leu Ala Trp Ala Glu Asp Pro Ala Trp Ala
            20                  25                  30

His Gly Gly Gly Leu Tyr His Ile Arg Cys Asp Tyr Arg Leu Met Ile
        35                  40                  45

Asp Asn Leu Met Asp Leu Thr His Glu Thr
    50                  55

<210> SEQ ID NO 20
<211> LENGTH: 58
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 20

Arg Tyr Gly Phe Ile Trp Val Trp Pro Gly Asp Pro Glu Gln Ala Asp
 1               5                  10                  15

Pro Ala Arg Ile His His Leu Glu Trp Ala Glu Ser Glu Ala Trp Ala
            20                  25                  30

Tyr Gly Gly Gly Leu Tyr His Ile Gln Cys Asp Tyr Arg Leu Met Ile
        35                  40                  45

Asp Asn Leu Met Asp Leu Thr His Glu Thr
    50                  55

<210> SEQ ID NO 21
<211> LENGTH: 58
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 21

Arg His Gly Phe Ile Trp Val Trp Pro Gly Asp Ala Glu Gln Ala Asp
 1               5                  10                  15

Pro Asp Gln Ile Pro Glu Leu His Trp Ala Asn Asp Pro Glu Trp Ala
            20                  25                  30

Tyr Gly Gly Gly Leu Tyr His Ile Asn Cys Asp Tyr Arg Leu Met Ile
        35                  40                  45

Asp Asn Leu Met Asp Leu Thr His Glu Thr
     50                  55

<210> SEQ ID NO 22
<211> LENGTH: 58
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Arg His Arg Phe Val Trp Leu Trp Met Gly Asp Pro Val Leu Ala Asp
 1               5                  10                  15

Pro Ala Leu Val Pro Asp Met His Trp Asn Asp Pro Ala Trp Ala
            20                  25                  30

Gly Asp Gly Lys Thr Ile Tyr Ala Lys Cys Asp Trp Arg Leu Val Val
        35                  40                  45

Asp Asn Leu Met Asp Leu Thr His Glu Thr
     50                  55

<210> SEQ ID NO 23
<211> LENGTH: 58
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Arg His Arg Tyr Ile Trp Leu Trp Met Gly Asp Pro Ala Leu Ala Asp
 1               5                  10                  15

Pro Ala Leu Val Pro Asp Met His Trp Asn His Asp Pro Ala Trp Ala
            20                  25                  30

Gly Asp Gly Lys Thr Ile Arg Val Asn Cys Asp Tyr Arg Leu Val Leu
        35                  40                  45

Asp Asn Leu Met Asp Leu Thr His Glu Thr
     50                  55

<210> SEQ ID NO 24
<211> LENGTH: 433
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
agatcttgag ccaatcaaag aggagtgatg tagacctaaa gcaataatgg agccatgacg      60
taagggctta cgcccatacg aaataattaa aggctgatgt gacctgtcgg tctctcagaa    120
```

```
cctttacttt ttatgtttgg cgtgtatttt taaatttcca cggcaatgac gatgtgaccc      180
aacgagatct tgagccaatc aaagaggagt gatgtagacc taaagcaata atggagccat      240
gacgtaaggg cttacgccca tacgaaataa ttaaaggctg atgtgacctg tcggtctctc      300
agaaccttta cttttatat ttggcgtgta tttttaaatt tccacggcaa tgacgatgtg       360
acctgtgcat ccgctttgcc tataaataag ttttagtttg tattgatcga cacggtcgag      420
aagacacggc cat                                                        433
```